(12) United States Patent
Reinherz et al.

(10) Patent No.: US 7,091,330 B2
(45) Date of Patent: Aug. 15, 2006

(54) CLONING AND CHARACTERIZATION OF A CD2 BINDING PROTEIN (CD2BP2)

(75) Inventors: Ellis L. Reinherz, Lincoln, MA (US); Christian Freund, Berlin (DE); Jing Li, Lynnfield, MA (US); Kazuhisa Nishizawa, Tokyo (JP); Gerhard Wagner, Brookline, MA (US)

(73) Assignees: Dana-Farber Cancer Institute, Inc., Boston, MA (US); President and Fellows of Harvard College, Cambridge, MA (US)

( * ) Notice: Subject to any disclaimer, the term of this patent is extended or adjusted under 35 U.S.C. 154(b) by 520 days.

(21) Appl. No.: 09/873,106

(22) Filed: Jun. 1, 2001

(65) Prior Publication Data

US 2002/0127657 A1 Sep. 12, 2002

Related U.S. Application Data

(63) Continuation of application No. PCT/US99/26993, filed on Nov. 15, 1999.

(60) Provisional application No. 60/115,647, filed on Jan. 13, 1999, provisional application No. 60/111,007, filed on Dec. 4, 1998.

(51) Int. Cl.
C12P 21/02 (2006.01)
C12N 15/12 (2006.01)

(52) U.S. Cl. .................... 536/23.5; 435/69.1; 435/325; 435/320.1

(58) Field of Classification Search ............... 536/23.1, 536/23.5; 435/6.91, 325, 320.1
See application file for complete search history.

(56) References Cited

FOREIGN PATENT DOCUMENTS

WO WO 90/13644 9/1990

OTHER PUBLICATIONS

Seed et al (PNAS 84(10):3365-3369 (1987) ).*
Percy C (submitted to the EMBL data Library on Oct. 1996) as evidenced by NCBI blast search.*
Alcover, Andres et al., "The T11 glycoprotein is functionally linked to a calcium channel in precursor and mature T-lineage cells," *Proc. Natl. Acad. Sci. USA* 83:2614-2618 (1986).
Bell, Gregory M. et al., "The SH3 Domain of p56[lck] Binds to Proline-rich Sequences in the Cytoplasmic Domain of CD2," *J. Exp. Med.* 183:169-178 (1996).
Bierer, Barbara E. et al., "The Biologic Roles of CD2, CD4, and CD8 in T-cell Activation," *Ann. Rev. Immunol.* 7:579-599 (1989).
Bierer, Barbara E. et al., "Partial Deletions of the Cytoplasmic Domain of CD2 Result in a Partial Defect in Signal Transduction," *J. of Immunology* 144(3) :785-789 (1990).
Bork, Peer and Sudol, Marius, "The WW domain: a signaling site in dystrophin?" *TIBS* 19 (12) :531-533 (1994).
Boussiotis, Vassiliki A. et al., "CD2 is Involved in Maintenance and Reversal of Human Allontigen-specific Clonal Anergy," *J. Exp. Med.* 180 : 1665-1673 (1994).
Chang, Hsiu-Ching et al., "Dissection of the Human CD2 Intracellular Domain," *J. Exp. Med.* 169:2073-2083 (1989).
Chang, Hsiu-Ching et al., "Involvement of the PPPGHR Motif in T Cell Activation Via CD2," *J. Exp. Med.* 172:351-355 (1990).
Gassmann, Martin et al., "Identification of a signaling complex involving CD2, ʃ chain and p59[fyn] in T lymphocytes," *Eur. J. Immunol.* 24:139-144 (1994).
Gollob, Jared A. et al., "Molecular Interaction Between CD58 and CD2 Counter-Receptors Mediates the Ability of Monocytes to Augment T Cell Activation by IL-12," *J. of Immunology* 157:1886-1893 (1996).
Gollob, Jared A. et al., "CD2 Regulates Responsiveness of Activated T Cells to Interleukin 12," *J. Exp. Med.* 182:721-731 (1995).
He, Qi et al., "A Role in Transmembrane Signaling for the Cytoplasmic Domain of the CD2 T Lymphocyte Surface Antigen," *Cell* 54:979-984 (1988).
Li, Jing et al., "A cdc15-like adaptor protein (CD2BP1) interacts with the CD2 cytoplasmic domain and regulates CD2-triggered adhesion," *EMBO Journal* 17(24) : 7320-7336 (1998).
Lillie, Sue H. and Brown, Susan S., "Suppression of a myosin defect by a kinesin-related gene," *Nature* 356:358-361 (1992).
Macias, Maria J. et al., "Structure of the WW domain of a kinase-associated protein complexed with a proline-rich peptide," *Nature* 382:646-649 (1996).
Moingeon, Philippe et al., "The Structural Biology of CD2," *Immunological Reviews* 111:111-144 (1989).
Musacchio, Andrea et al., "Structure and Function of the SH3 Domain," *Prog. Biophys. Molec. Biol.* 61:283-297 (1994).
Nishizawa, Kazuhisa et al., "Identification of a proline-binding motif regulating CD2-triggered T lymphocyte activation," *Proc. Natl. Acad. Sci. USA* 95:14897-14902 (1998).
Nolan, Garry P. et al., "Fluorescence-activated cell analysis and sorting of viable mammalian cells based on β-D-galactosidase activity after transduction of *Escherichia coli* lacZ," *Proc. Natl. Acad. Sci USA* 85:2603-2607 (1988).
Nguyen, Jack T. et al., "Exploiting the Basis of Proline Recognition by SH3 and WW Domains: Design of N-Substituted Inhibitors," *Science* 282:2088-2092 (1998).
Pawson, Tony, Protein modules and signalling networks, *Nature* 373:573-580 (1995).
Reem, Gabrielle H. et al., "Lymphokine Synthesis is Induced in Human Thymocytes by Activation of the CD 2 (T11) Pathway," *J. of Immunology* 139 (1) :130-134 (1987).

(Continued)

*Primary Examiner*—Christina Chan
*Assistant Examiner*—F. Pierre VanderVegt
(74) *Attorney, Agent, or Firm*—Hamilton, Brook, Smith & Reynolds, P.C.

(57) ABSTRACT

A human CD2 cytoplasmic tail binding protein, CD2BP2, is described, as well as the nucleic acids encoding the protein. Also described are expression vectors and recombinant host cells comprising nucleic acids encoding the CD2BP2 protein, and methods of use for the CD2BP2 protein and nucleic acids encoding the CD2BP2 protein.

17 Claims, 13 Drawing Sheets

OTHER PUBLICATIONS

Ren, Ruibao et al., "Identification of a Ten-Amino Acid Proline-Rich SH3 Binding Site," *Science* 259:1157-1161 (1993).

Semnani, R. Tolouei et al., "Acquisition of Interleukin-5 Secretion by Human Naive T-Helper Cells is Regulated by Distinct Signals from both the T-Cell Receptor/CD3 Complex and CD2," *Scand. J. Immunol.* 47:436-443 (1998).

Springer, Timothy A., "Adhesion receptors of the immune system," *Nature* 346:425-434 (1990).

Sudol, Marius, "Structure and Function of the WW Domain," *Prog. Biophys. Molec. Biol.* 65 (½) :113-132 (1996).

Sunder-Plassmann, Raute and Reinherz, Ellis L., "A $p56^{lck}$ -independent Pathway of CD2 Signaling Involves Jun Kinase," *J. Biol. Chem.* 273 (37) :24249-24257 (1998).

Targan, Stephan R. et al., "Definition of a Lamina Propria T Cell Responsive State," *J. of Immunology* 154:664-675 (1995).

Yu, Hongtao et al., "Solution Structure of the SH3 Domain of Src and Identification of its Ligand-Binding Site," *Science* 258:1665-1668 (1992).

Burkhardt, Anne L. and Bolen, Joseph B., "Assessment of the Effects of Tyrosine Protein Kinase Inhibitors," *Current Protocols in Immunology*, eds. J.E. Coligan et al., John Wiley and Sons, vol. 2, pp. 11.5.1-11.5.6 (1993).

Mizukoshi, Noriko et al., "The complete sequence of African horsesickness virus serotype 4 (vaccine strain) RNA segment 5 and its predicted polypeptide compared with NS1 of bluetongue virus," *J. Gen. Virology* 73:2425-2428 (1992).

\* cited by examiner

FIG. 1A

```
    AGTCCTCTTCCGGGTGATGGCGGCGGGTGCCCCGGATGTAGCCCTGGCGCAAGCATCTCT
    TCTTTTTTCCACCTCGCCTTCCGCGGATTCCCAGCTTGAGAAACACCTCTTTGCCCCGTC
  1 ATGCCAAAGAGGAAAGTGACCTTCCAAGGCGTGGGAGATGAGGAGGATGAGGATGAAATC
    M  P  K  R  K  V  T  F  Q  G  V  G  D  E  E  D  E  D  E  I
 61 ATTGTCCCCAAGAAGAAGCTGGTGGACCCTGTGGCTGGGTCAGGGGGTCCTGGGAGCCGC
    I  V  P  K  K  K  L  V  D  P  V  A  G  S  G  G  P  G  S  R
121 TTTAAAGGCAAACACTCTTTGGATAGCGATGAGGAGGAGGATGATGATGATGGGGGGTCC
    F  K  G  K  H  S  L  D  S  D  E  E  E  D  D  D  D  G  G  S
181 AGCAAATATGACATCTTGGCCTCAGAGGATGTAGAAGGTCAGGAGGCAGCCACACTCCCC
    S  K  Y  D  I  L  A  S  E  D  V  E  G  Q  E  A  A  T  L  P
241 AGCGAGGGGGGTGTTCGGATCACACCCTTTAACCTGCAGGAGGAGATGGAGGAAGGCCAC
    S  E  G  G  V  R  I  T  P  F  N  L  Q  E  E  M  E  E  G  H
301 TTTGATGCCGATGGCAACTACTTCCTGAACCGGGATGCTCAGATCCGAGACAGCTGGCTG
    F  D  A  D  G  N  Y  F  L  N  R  D  A  Q  I  R  D  S  W  L
361 GACAACATTGACTGGGTGAAGATCCGGGAGCGGCCACCTGGCCAGCGCCAGGCCTCAGAC
    D  N  I  D  W  V  K  I  R  E  R  P  P  G  Q  R  Q  A  S  D
421 TCGGAGGAGGAGGACAGCTTGGGCCAGACCTCAATGAGTGCCCAAGCCCTCTTGGAGGGA
    S  E  E  E  D  S  L  G  Q  T  S  M  S  A  Q  A  L  L  E  G
481 CTTTTGGAGCTCCTATTGCCTAGAGAGACAGTGGCTGGGCACTGAGGCGTCTGGGGGCC
    L  L  E  L  L  L  P  R  E  T  V  A  G  A  L  R  R  L  G  A
541 CGAGGAGGAGGCAAAGGGAGAAAGGGGCCTGGCAACCCAGTTCCCCTCAGCGCCTGGAC
    R  G  G  G  K  G  R  K  G  P  G  Q  P  S  S  P  Q  R  L  D
601 CGGCTCTCCGGGTTGGCCGACCAGATGGTGGCCCGGGGCAACCTTGGTGTGTACCAGGAA
    R  L  S  G  L  A  D  Q  M  V  A  R  G  N  L  G  V  Y  Q  E
661 ACAAGGGAACGGTTGGCTATGCGTCTGAAGGGTTTGGGGTGTCAGACCCTAGGACCCCAC
    T  R  E  R  L  A  M  R  L  K  G  L  G  C  Q  T  L  G  P  H
721 AATCCCACACCCCCACCCTCCCTGGACATGTTCGCTGAGGAGTTGGCCGGAGGAGGAACTG
    N  P  T  P  P  P  S  L  D  M  F  A  E  E  L  A  E  E  L
781 GAGACCCCAACCCCTACCCAGAGAGGAGAAGCAGAGTCGCGGGGAGATGGTCTGGTGGAT
    E  T  P  T  P  T  Q  R  G  E  A  E  S  R  G  D  G  L  V  D
841 GTGATGTGGGAATATAAGTGGGAGAACACGGGGGATGCCGAGCTGTATGGGCCCTTCACC
    V  M  W  E  Y  K  W  E  N  T  G  D  A  E  L  Y  G  P  F  T
901 AGCGCCCAGATGCAGACCTGGGTGAGTGAAGGCTACTTCCCGGACGGTGTTTATTGCCGG
    S  A  Q  M  Q  T  W  V  S  E  G  Y  F  P  D  G  V  Y  C  R
961 AAGCTGGACCCCCCTGGTGGTCAGTTCTACAACTCCAAACGCATTGACTTTGACCTCTAC
    K  L  D  P  P  G  G  Q  F  Y  N  S  K  R  I  D  F  D  L  Y*
1021 ACCTGAGCCTGCTGGGGGCCCAGTTTGGTGGGCCCTTCTTTCCTGGACTTTGTGGAGGAG
     T
1081 GCACCAAGTGTCTCAGGCAGCGAGGAAATTGGAGGCCATTTTTCAGTCAATTTCCCTTTC
1141 CC(AATAAA)GCCTTTAGTTGTGTAAAAAAAAAAAAAAAA
```

FIG. 1B

```
CD2BP2 291-317  G - D A E L Y G P F T S A Q M Q T W V S E G Y F P D G
C. el. (z81109)     G P D S E K Y G P Y M S K D M L F W L Q A G Y F N D G
C. el. (u23147)     D P T E T R R G P F P K D Q M N V W F K A G Y F T D E
C. el. (p34520)     D D R G T V Q G P Y G A S T V L D W Y Q K G Y F S D N
S. ce. (SMY2)       D T Q G Q I H G P F T T Q M M S Q W Y I G G Y F A S T
S. ce. (s61962)     D S N G N I Q G P F G T N N M S Q W Y Q G G Y F T P T
                              ( G P F         M       W     G Y F )
                                  Y           V
```

FIG. 1C

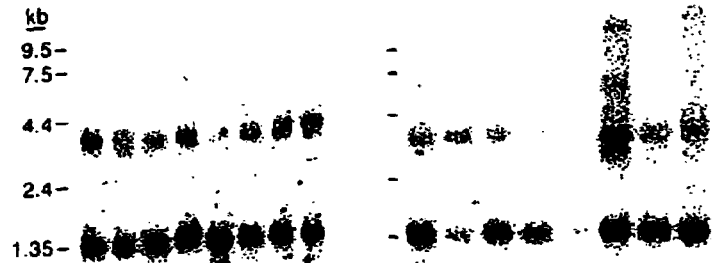

| | | | Binding with CD2 tail |
|---|---|---|---|
| CD2BP2 | 1 ———————————————— 341 | | ++++ |
| CD2BP2₁₂₉₋₃₄₁ | 129 ———————— 341 | | ++++ |
| CD2BP2₁₂₉₋₂₈₇ | 129 ——————— 287 | | − |
| CD2BP2₁₂₉₋₂₅₄ | 129 ———— 254 | | − |
| CD2BP2₂₂₅₋₃₄₁ | 225 —————— 341 | | ++++ |
| CD2BP2₂₅₆₋₃₄₁ | 256 ————— 341 | | ++++ |
| CD2BP2 256-341Δ297-313 | 256  296  314  341 (deletion) | | − |
| CD2BP2 256-341W307A | 256  297 A 313  341 | | − |
| CD2BP2 256-341G311A | 256  A  341 | | − |
| CD2BP2 256-341Y312A | 256  A  341 | | − |
| CD2BP2 256-341F313A | 256  A  341 | | − |
| CD2BP2 256-332 | 256 ————— 332 Δ9 residues | | − |
| CD2BP2 256-338 | 256 ————— 338 Δ3 residues | | ++ |

FIG. 3A

CLONING AND CHARACTERIZATION OF A CD2 BINDING PROTEIN (CD2BP2)

RELATED APPLICATIONS

This application is a continuation of International Application No. PCT/US99/26993 which designated the United States and was filed on Nov. 15, 1999, published in English, which claims the benefit of U.S. Provisional Application Nos. 60/111,007, filed Dec. 4, 1998 and 60/115,647, filed Jan. 13, 1999, the entire contents of which are incorporated herein by reference.

BACKGROUND OF THE INVENTION

The human CD2 molecule is found on virtually all T cells and thymocytes as well as natural killer cells, and it binds to the surface glycoprotein CD58 which is present on many cell types including antigen presenting cells. Human CD2 functions to facilitate both adhesion and activation of T lymphocytes on binding to CD58 (Bierer et al., *Annu. Rev. Immunol.* 7:579–599 (1989); Moingeon et al., *Immunol. Rev.* 111:111–133 (1989); Springer, *Nature (London)* 346:425–434 (1990)). Moreover, the binding of CD58 to CD2 augments interleukin (IL)-12-driven T cell responsiveness (Gollob et al., *J. Exp. Med.* 182:721–731 (1995); Gollob et al., *J. Immunol.* 157:1886–1893 (1996)) and initiates reversal of the anergic state (Boussiotis et al, *J. Exp. Med.* 180:1665–1673 (1994)). Although the important contribution of the cytoplasmic tail of CD2 to T cell activation has been studied in both rodents and humans (Chang et al., *J. Exp. Med.* 169:2073–2083 (1989); Chang et al., *J. Exp. Med.* 172:351–355 (1990); Bierer et al., *J. Immunol.* 144: 785–789 (1990); He et al., *Cell* 54:979–984 (1988)), the mechanisms by which the CD2 tail mediates those functions are not clear.

SUMMARY OF THE INVENTION

An intracellular protein termed CD2 binding protein 2 (CD2BP2), which binds to a site containing two PPPGHR (SEQ ID NO: 10) segments within the cytoplasmic region of CD2, has been identified as described herein. Mutagenesis and NMR analysis demonstrated that the CD2 binding region of CD2BP2 includes a 17-amino acid motif (GP[Y/F]xxxx[M/V]xxWxxxGYF (SEQ ID NO: 9)), which is also found in several yeast and *Caenorhabditis elegans* proteins of unknown function. In Jurkat T cells, over-expression of the isolated CD2BP2 domain binding to CD2 enhances the production of interleukin 2 on crosslinking of CD2 but not the T cell receptor. Hence, a proline-binding module distinct from SH3 and WW domains regulates protein-protein interactions. This proline-rich sequence binding domain, which contains a conserved Gly-Thy-Phe motif, has been named herein the GYF domain and its solution structure determined.

Thus, the invention relates to isolated CD2BP2 protein, or an active derivative or fragment thereof having CD2BP2 protein activity. In one embodiment, the protein is a derivative possessing substantial sequence identity with SEQ ID NO: 2. In a preferred embodiment, the protein has the amino acid sequence of SEQ ID NO: 2.

The invention also relates to an isolated peptide consisting essentially of the amino acid sequence of SEQ ID NO: 3, SEQ ID NO: 9 or SEQ ID NO: 10.

The invention further relates to an isolated nucleic acid molecule which encodes a CD2BP2 protein, or an active derivative or fragment of said protein having CD2BP2 protein activity, or the complement of said nucleic acid molecule. In one embodiment, the CD2BP2 protein is a derivative possessing substantial sequence identity with SEQ ID NO: 2. In another embodiment, the nucleic acid molecule has the same nucleotide sequence as the endogenous gene encoding a CD2BP2 protein. In a preferred embodiment, the nucleic acid molecule comprises the nucleotide sequence of SEQ ID NO:1.

The invention also relates to an isolated nucleic acid molecule consisting essentially of a nucleotide sequence encoding the amino acid sequence of SEQ ID NO: 3, the amino acid sequence of SEQ ID NO: 9 or the amino acid sequence of SEQ ID NO: 10.

The invention further relates to nucleic acid constructs and recombinant host cells comprising the isolated nucleic acid molecules described herein operably linked to a regulatory sequence.

The invention also relates to a method for preparing a CD2BP2 protein, or an active derivative of fragment thereof, comprising culturing a recombinant host cell according to the invention.

The invention further pertains to an antibody which selectively binds to isolated CD2BP2 protein, or to an active derivative or fragment thereof. In one embodiment, the CD2BP2 protein has the amino acid sequence of SEQ ID NO: 2.

The invention also relates to a method for assaying the presence of CD2BP2 protein in a cell, comprising contacting said cell with an antibody of the invention. For example, the cell can be in a tissue sample.

The invention pertains to an assay for identifying an agent which alters (e.g., inhibits or enhances) activity of CD2BP2 protein, comprising contacting a composition comprising the CD2BP2 protein, or an active derivative or fragment thereof, with an agent to be tested; and identifying alteration (e.g., inhibition or enhancement) of CD2BP2 protein activity. The invention also includes novel agents which alter activity of CD2BP2 protein identified according to the assays described herein. The invention further pertains to methods of altering (e.g., inhibiting or enhancing) CD2BP2 protein activity, comprising contacting said CD2BP2 protein with an agent that alters activity of the CD2BP2 protein.

The invention also relates to methods of identifying an agent which modulates signal transduction or cell adhesion, comprising contacting a composition comprising the CD2BP2 protein, or an active derivative or fragment thereof, with an agent to be tested; and identifying modulation of CD2BP2 protein activity, wherein the presence of modulation of CD2BP2 protein activity indicates that the agent modulates signal transduction or cell adhesion. The invention further pertains to a method of modulating signal transduction or cell adhesion, comprising-contacting CD2BP2 protein with an agent that modulates CD2BP2 protein activity.

The invention also includes an assay for identifying an agent which alters (e.g., enhances or inhibits) CD2-triggered IL-2 production, comprising contacting a composition comprising the CD2BP2 protein, or an active derivative or fragment thereof, with an agent to be tested; and identifying alteration of IL-2 production. The invention further includes novel agents which alter CD2-triggered IL-2 production identified according to the assays described herein. The invention also relates to a method of altering CD2-triggered IL-2 production, comprising contacting a cell comprising CD2BP2 protein with an agent that alters CD2-triggered IL-2 production.

The invention also relates to a method of targeting an agent to a CD2 molecule in a cell, comprising linking the agent with CD2BP2 protein or an active derivative or fragment thereof having CD2BP2 activity.

The invention further pertains to an isolated nucleic acid molecule comprising a nucleotide sequence encoding the amino acid sequence of SEQ ID NO: 3, 9 or 10, wherein said nucleic acid molecule does not naturally comprise said nucleotide sequence, and to proteins encoded by these nucleic acid molecules.

The invention also relates to a method of enhancing protein-protein interactions, comprising contacting a protein encoded by an isolated nucleic acid molecule comprising a nucleotide sequence encoding the amino acid sequence of SEQ ID NO: 3 or 9, wherein said nucleic acid molecule does not naturally comprise said nucleotide sequence, with a protein encoded by an isolated nucleic acid molecule comprising a nucleotide sequence encoding the amino acid sequence of SEQ ID NO: 10, wherein said nucleic acid molecule does not naturally comprise said nucleotide sequence.

The invention further relates to a method of enhancing protein-protein interactions, comprising contacting a protein comprising the amino acid sequence of SEQ ID NO: 3 or 9, wherein said protein does not naturally comprise said amino acid sequence, with a protein comprising the amino acid sequence of SEQ ID NO: 10, wherein said protein does not naturally comprise said amino acid sequence.

BRIEF DESCRIPTION OF THE DRAWINGS

The file of this patent contains three drawings executed in color. Copies of this patent with the color drawings will be provided by the Patent and Trademark Office upon request and payment of the necessary fee.

FIGS. 1A–1C show the CD2BP2 sequence, binding motif and RNA blot analysis of CD2BP2 expression.

FIG. 1A shows the nucleotide sequence (SEQ ID NO: 1) and predicted amino acid sequence (SEQ ID NO: 2) of CD2BP2. The 17-residue segment showing homology with other proteins is shaded. The arrow defines the start of the smallest C-terminal CD2BP2 segment binding to CD2 as shown by mutation analysis using a yeast two-hybrid system. The asterisk indicates the tyrosine residue which is a potential phosphorylation site. The polyadenylation signal is circled. The two clones obtained from the yeast two-hybrid system have an identical overlapping sequence of 768 base pairs (bp) with the longer of the two clones extending 408 bp further 5'. Seven independent RACE clones were sequenced to determine the upstream region from bp −24 to −120.

FIG. 1B shows an alignment of the motif segment residing between amino acids 291–317 (SEQ ID NO: 3) of CD2BP2 with sequences from several other proteins (SEQ ID NOS: 4–8, respectively). To identify local homologies, segments of the CD2BP2 amino acid sequence were subjected to the standard BLAST search (Altschul, *Nucleic Acids Res.* 25:3389–3402 (1997)) against SWISSPROT and translated sequences of the GenBank data, using a sliding window of 50 residues over the sequence with a pitch of 20 residues. All of the sequences that meet the consensus 17-residue motif (GP[F/Y]xxxx[M/V]xxWxxxGYF; SEQ ID NO: 9) were aligned with the use of MEGALIGN (DNAstar, Madison, Wis.). The origin (*C.el.* indicates *C. elegans*; *S.ce.* indicates *S. cerevisiae*) and the accession number or name of each locus is shown in parentheses. SMY2 was cloned as a suppressor of the defect in myosin (Lillie and Brown, *Nature (London)* 356:358–361 (1992)).

FIG. 1C shows RNA blot analysis of CD2BP2 expression.

FIG. 2A shows a Western blot analysis of lysates from parental cells or cells transfected with the cDNA encoding the CD2BP2 protein tagged with an N-terminal FLAG epitope. The FLAG epitope was detected on a protein migrating with apparent MW of 50 KD. Lane 1 shows control untransfected COS7 cells; lane 2 shows transiently transfected COS7 cells; lane 3 shows control untransfected Jurkat (J77) cells; and lane 4 shows a representative stable Jurkat FLAG-tagged CD2BP2 cDNA transformant. FIG. 2B shows the interaction between CD2BP2 and CD2 in COS7 cells. COS7 cells were transfected with FLAG-CD2BP2 cDNA (lane 1), with FLAG-CD2BP2 and a human CD2 cDNA (lanes 2 and 3), or with FLAG-CD2BP2 and a human CD4 cDNA (lanes 4 and 5), then were lysed and immunoprecipitated with the anti-FLAG mAb M2 (lanes 3 and 5), with anti-CD2 mAb (anti-T11$_1$)(lanes 1 and 2), or with anti-CD4 mAb (19Thy5D7) (lane 4). Subsequently, the amount of FLAG-CD2BP2 in the immunoprecipitates was assayed by anti-FLAG mAb M2 Western blotting. FIG. 2C shows binding of CD2BP2 to CD2 in Jurkat transformants. Lysates from control Jurkat cells (lane 2) and Jurkat cells stably transfected with FLAG-CD2BP2 cDNA (lanes 1 and 3–5) were immunoprecipitated with anti-CD2 mAb anti-T11$_1$ (lane 1), anti-FLAG M2 mAb (lanes 2 and 3), anti-CD4 mAb (lane 4), or the irrelevant leucine zipper mAb 2H11 (lane 5), and the associated CD2 protein was detected by using the M32 anti-CD2 rabbit heteroantisera. Standard protocol for enhanced chemiluminescence was used.

FIGS. 3A–3B show mutational analysis of CD2 and CD2BP2 interaction sites. For each construct, the strength of interaction was scored by yeast two-hybrid analysis. FIG. 3A shows the results when CD2BP2 and its derivatives were tested for their binding to the CD2 cytoplasmic region (CD2$_{221-327}$). Note that the 17 residues highlighted in FIG. 1A are residues 297–313. The amino acid numbers corresponding to the boundaries of each fragment are shown. The nomenclature denotes the residues that were contained or modified in each construct.

FIG. 3B shows the results when human CD2 and its derivatives tested for binding with CD2BP2. In the schematic diagram, D1 and D2 represent domains 1 and 2 of the extracellular region of CD2, respectively. TM indicates the transmembrane segment; MPR indicates the membrane proximal region. The three proline rich regions conserved among all species characterized to date are underlined. Binding was scored as described herein.

FIG. 5A shows the pBI-G vector system. This vector has a bidirectional promoter (Pbi-1) that allows the expression of two genes on either side of the promoter. Thus, both CD2BP2$_{225-341}$ and β-gal are expressed, with the latter functioning as the reporter. FIG. 5B shows the sorting of β-gal positive and negative populations of Jurkat cells after transient CD2BP2$_{225-341}$ transfection. Presorted and sorted populations are shown as fluorescence histograms of cell number on the y axis versus log fluorescence of the cleaved β-gal substrate fluorescence-2-galactopyranoside on the x axis. FIG. 5C shows CD2-triggered $Ca^{2-}$ flux in β-gal- and β-gal+ cells. $Ca^{2-}$ influx was measured as described in Chang et al. (*J. Exp. Med.* 169:2073–2083 (1989); Chang et al., *J. Exp. Med.* 172: 351–355 (1990)). A filled arrowhead indicates the time point when cells were stimulated with anti-T11$_2$ and T11$_3$ (ascites 1:200 dilution). FIG. 5D shows the effect of the expression vector pBI-G, pBI-G-CD2BP2$_{225\text{-}341}^{sense}$ and pBI-G-CD2BP$_{129\text{-}341}^{antisense}$ on IL-2 production following CD2 crosslinking. The height of the bars shows the ratio of IL-2 produced from β-gal+ versus β-gal− subpopulations isolated by cell sorting from the same transient transfection. Results from two representative experiments are shown. For statistical analysis, at test was used to examine the difference between the pairwise data (such as those from galactosidase [gal] positive [+] and negative [−] cells from each experiment set). This test showed clearly significant differences between gal+ and gal− cells on transfection of CD2BP2$_{225\text{-}341}^{sense}$ ($p<0.001$) and CD2BP2$_{129\text{-}341}^{antisense}$ ($P<0.01$), but no significant difference on transfection with the vector pBI-G ($P>0.1$). FIG. 5E shows the effect of the expression of pBI-G-CD2BP2$_{225\text{-}341}^{sense}$ on IL-2 production of unstimulated Jurkat-tTA or Jurkat-tTA triggered by CD2 crosslinking or CD3 crosslinking. β-gal+ (solid bar) and β-gal− (hatched bar) cells were stimulated, as indicated, in parallel. One of two representative experiments is shown in which IL-2 levels were measured in triplicate, and the mean±SD is displayed. The mean and SD of the data regarding the amount of IL-2 produced by β-gal negative (positive) cells are as follows: with no stimulation, 25±18 (28±10); CD2 stimulation, 480±159 (870±83.5); and CD3 stimulation, 201±58.1 (215±54.0).

FIG. 7A shows a ribbon representation of the GYF domain of CD2BP2 using the program (Koradi, et al., *J. Mol. Graphics* 14:51–55 (1996)). Secondary structure elements are colored and residue numbers define the beginning and ends of the respective β-strands and helices. FIG. 7B shows a stereoview of a superposition of the best 16 NMR structures of the backbone (N, Cα and C') atoms of the CD2BP2 GYF domain generated using InsightII (Molecular Simulations). Regular secondary structure elements are color coded as in FIG. 7A. The side-chains of conserved residues as defined by FIG. 6 are displayed in yellow and marked by residue type and sequence number. A potential site for tyrosine phosphorylation, Y61, is depicted in green. The main-chain atoms are superimposed against the energy-minimized average structure. The r.m.s.d. for all heavy atoms is 0.97 Å and 0.54 Å for the backbone atoms. Loop residues 10–15 and 44–49 are distant from the binding site and omitting these residues results in a r.m.s.d. of 0.89 Å for all heavy atoms and 0.35 Å for the backbone atoms.

FIG. 8A shows the binding site of the CD2BP2 GYF domain as mapped by the NMR based titration experiment (green). Residues with a combined chemical shift change index greater than 0.7 (FIG. 6) were included in the binding site. The proline residues P19 and P35 of the GYF domain, which could not be observed in the $^{15}N$—$^1H$ correlation experiment used to identify the binding site, have been included in the binding surface, since each residue lies between two residues that show a large chemical shift change upon binding. W28 has also been included, because its side-chain NH group shifted significantly upon binding (Nishizawa, et al., *Proc. Natl. Acad. Sci. USA* 95:14897–14902 (1998)). FIG. 8B shows the representation of conserved residues of the GYF domain (yellow) according to FIG. 6. FIG. 8C shows the representation of the potential map of the surface of the GYF domain with acidic residues labeled (red).

DETAILED DESCRIPTION OF THE INVENTION

To define proteins interacting with the CD2 cytoplasmic region, a yeast two-hybrid system was used (Finley and Brent, *Interaction Trap Cloning with Yeast* (Oxford Univ. Press), NY (1995)), and eight clones were isolated from an activated human T cell cDNA library; these clones demonstrated strong interaction with the CD2 cytoplasmic tail. DNA sequencing showed that five clones contained SH3 domains (Ren et al., *Science* 259:1157–1161(1993); Musacchio et al., *Prog. Biophys. Mol. Biol.* 61:283–297 (1994)), one clone contained a WW domain (Bork and Sudol, *Trends Biochem. Sci.* 19:531–533 (1994)), and the remaining clones lacked both of these known domains. The latter two clones were derived from the same gene but differed in size. 5' RACE analysis (Frohman, *Methods Enzymol.* 218:340–356 (1993)) showed that the complete coding region of the gene product (termed CD2BP2) specifies a 341-amino acid polypeptide (FIG. 1A). Although standard BLAST homology search (Altschul, *Nucleic Acids Res.* 25:3389–3402 (1997)) with the entire sequence did not reveal any significant homology with entries in SWISSPROT and translated sequences of the GenBank database, the C-terminal region showed local homology with some *Caenorhabditis elegans* and yeast (*Saccharomyces cerevisiae*) proteins of unknown function. Sequence alignment identified 17 residues that are particularly conserved, comprising the following motif: GP[F/Y]xxxx[M/V]xxWxxxGYF (SEQ ID NO: 9) (FIG. 1B). It was also noted that a segment near the C-terminus contains a consensus site for potential tyrosine phosphorylation. RNA blot analysis indicates that CD2BP is expressed in a wide variety of organs as ~1.35- and 4-kilobase RNAs (FIG. 1C).

Figure 2A:
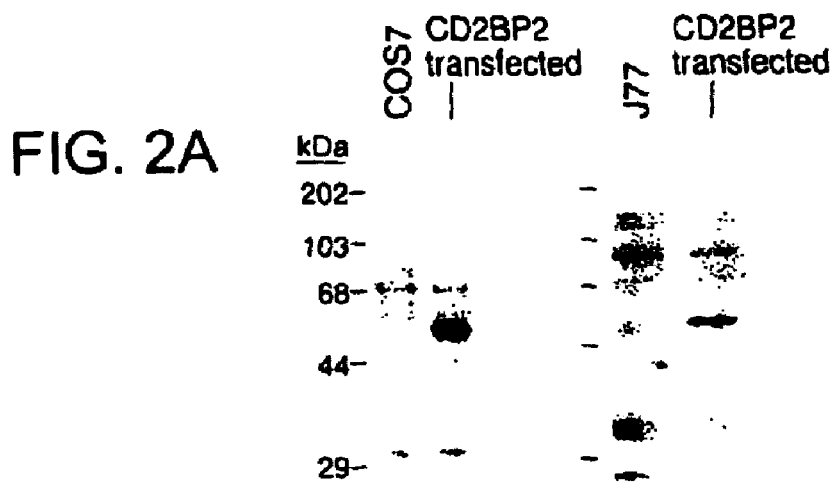
FIGS. 2A–2C show in vivo binding of CD2 to CD2BP2.

To characterize the nature and associations of the CD2BP2 protein, Jurkat cells (J77) and COS7 cells were transfected with the CD2BP2 cDNA tagged with a FLAG epitope. The apparent molecular size (~50 kDa) detected by anti-FLAG mAb Western blotting is larger in both cell types than that expected based on the theoretical molecular weight (molecular weight=37.6) (FIG. 2A). This anomalous mobility is likely a consequence of the acidic nature of the CD2BP2 protein (pH=~4.49).

Figure 2B:
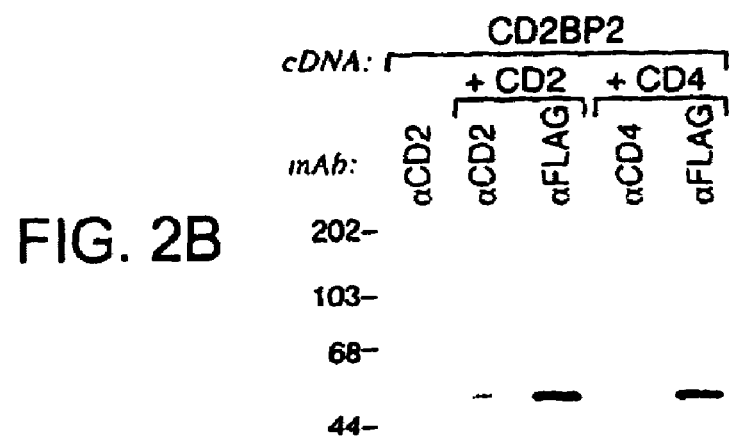

To determine whether CD2BP2 associates specifically with CD2, COS7 cells were cotransfected with FLAG-CD2BP2 and CD2 cDNA, or, as a control, CD4 cDNA. Subsequently, the CD2 protein was immunoprecipitated with anti-CD2 mAb and association with CD2BP2 examined by Western blotting with anti-FLAG mAb. As shown in FIG. 2B, FLAG-CD2BP2 specifically associates with CD2 (FIG. 2B, lane 2) but not with CD4 (FIG. 2B, lane 4). The amount of CD2BP2 associated with CD2, however, is only a fraction of the CD2BP2 protein expressed in the COS7 cells.

Figure 2C:
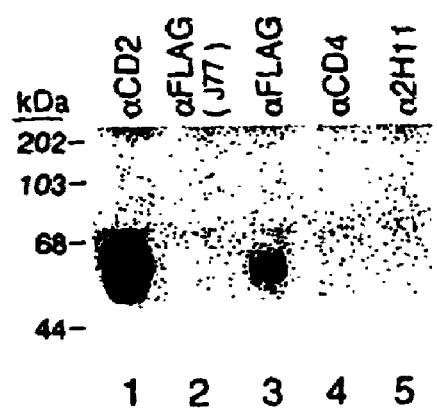

To determine next whether the interaction between CD2 and CD2BP2 could be detected in lymphoid cells, lysates of J77 FLAG-CD2BP2 transfectants were immunoprecipitated with anti-FLAG mAb followed by Western blotting with anti-CD2 heteroantisera (FIG. 2C). Although anti-FLAG mAb precipitated CD2 from the Jurkat cells transfected with FLAG-CD2BP2 (FIG. 2C, lane 3), anti-CD4 mAb (FIG. 2C, lane 4), and an irrelevant control mAb (anti-leucine zipper mAb 2H11) (FIG. 2C, lane 5), anti-CD8 (21 Thy2D3) and anti-HLA (W6-32) showed no significant CD2 coprecipitation. Moreover, in untransfected J77 cells, no CD2 was detected in the anti-FLAG mAb immunoprecipitate (FIG. 2C, lane 2).

Molecules such as lck and fyn, reported to bind to CD2, each contain SH3 domains (Ren et al., *Science* 259:1157–1161 (1993); Musacchio et al, *Prog. Biophys. Mol. Biol.* 61:283–297 (1994); Bell et al., *J. Exp. Med.* 183:169–178 (1997); Gassmann et al., *Eur. J. Immunol.* 24:139–144 (1994)). Because CD2BP2 possessed no known protein-protein interaction binding motif, CD2BP2 deletion mutants were generated and their ability to bind to CD2 in the yeast two-hybrid system was determined. All clones with N-terminal deletions (CD2BP2$_{129-134}$, CD2BP2$_{225-341}$, CD2BP2$_{256-341}$) showed binding activity, whereas two C-terminal deletion mutants tested (CD2BP2$_{129-287}$, CD2BP2$_{129-254}$) did not (FIG. 3A). This finding is of note because the shortest functional clone, CD2BP2$_{256-341}$, contains the motif identified by sequence homology (amino acids 297–317) (FIGS. 1A–1B). Consistent with the notion that the identified motif may be functionally relevant, a deletion clone lacking those 17 residues, CD2BP2$_{256-341\Delta297-313}$, failed to bind to CD2 as detected in complementation analysis.

To test further the functional importance of this segment, four alanine scanning mutants involving the most conserved residues were generated (W307A, G311A, Y312A, and F313A). Each mutation abolished detectable binding, suggesting that the 17-residue motif is critical for CD2 binding. To further delineate other regions of CD2BP2 responsible for the CD2 binding, two additional constructs whose C termini were truncated were also generated. Of note, with the three-residue C-terminal truncation (CD2BP2$_{256-338}$), interaction was weakened, whereas with the nine-residue truncation (CD2BP2$_{256-332}$), binding was no longer detectable. Collectively, these results support the idea that C-terminal residues of CD2BP2 may fold in such a way that they interact directly or indirectly with the 17-residue motif to mediate binding to CD2.

Figure 3B:
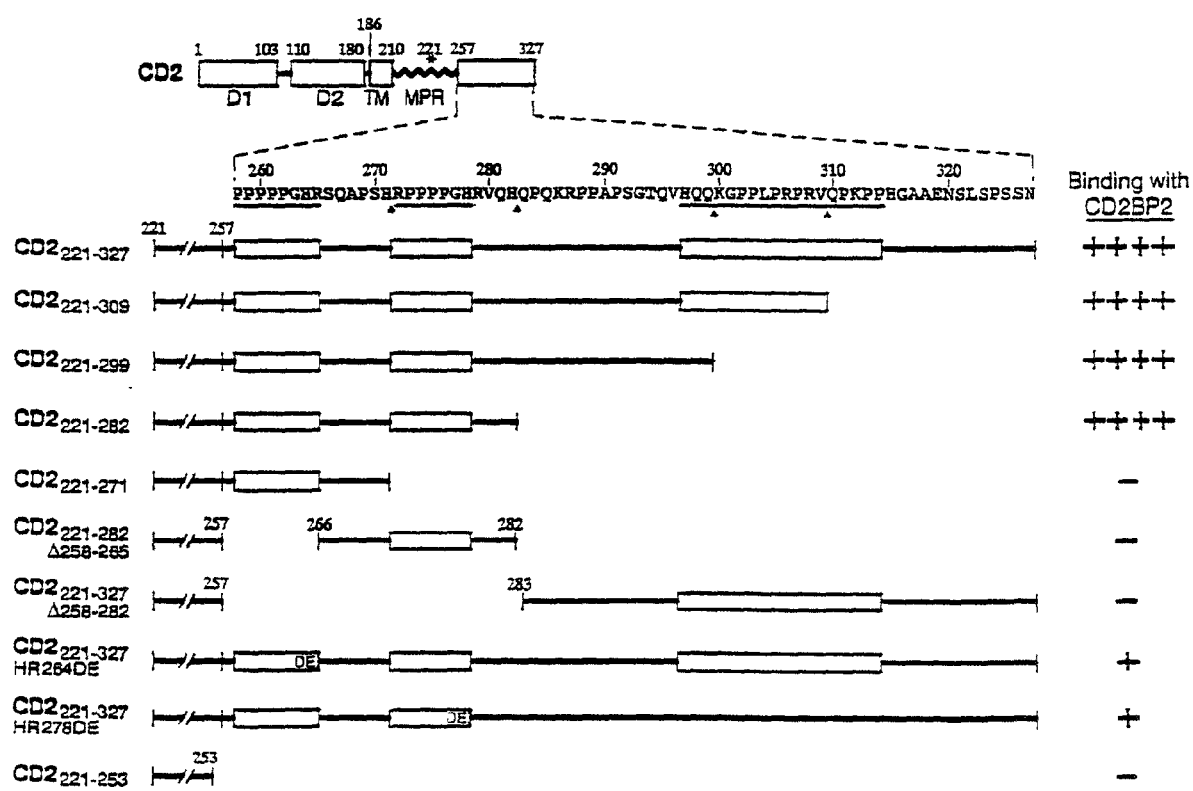

To map the CD2BP2 binding site on CD2, several CD2 cytoplasmic tail truncation mutants were generated for yeast two-hybrid analysis (FIG. 3B). Two deletion mutants, CD2$_{221-299}$ and CD2$_{221-282}$, lacking the conserved 18-amino acid C-terminal segment that binds to the SH3 domains of fyn and CD2BP 1, still maintained strong binding to CD2BP2. By contrast, when either of the two PPPGHR (SEQ ID NO: 10) sequences was deleted (e.g., CD2$_{221-271}$ or CD2$_{221-282\Delta258-265}$), binding was abolished. Moreover, mutation within either sequence (e.g., CD2$_{221-327HR264DE}$ or CD2$_{221-327H278DE}$) markedly attenuated binding. These data indicate that the two PPPGHR (SEQ ID NO: 10) sequences within the CD2$_{257-282}$ cytoplasmic tail segment mediate the binding to CD2BP2.

Figure 4:
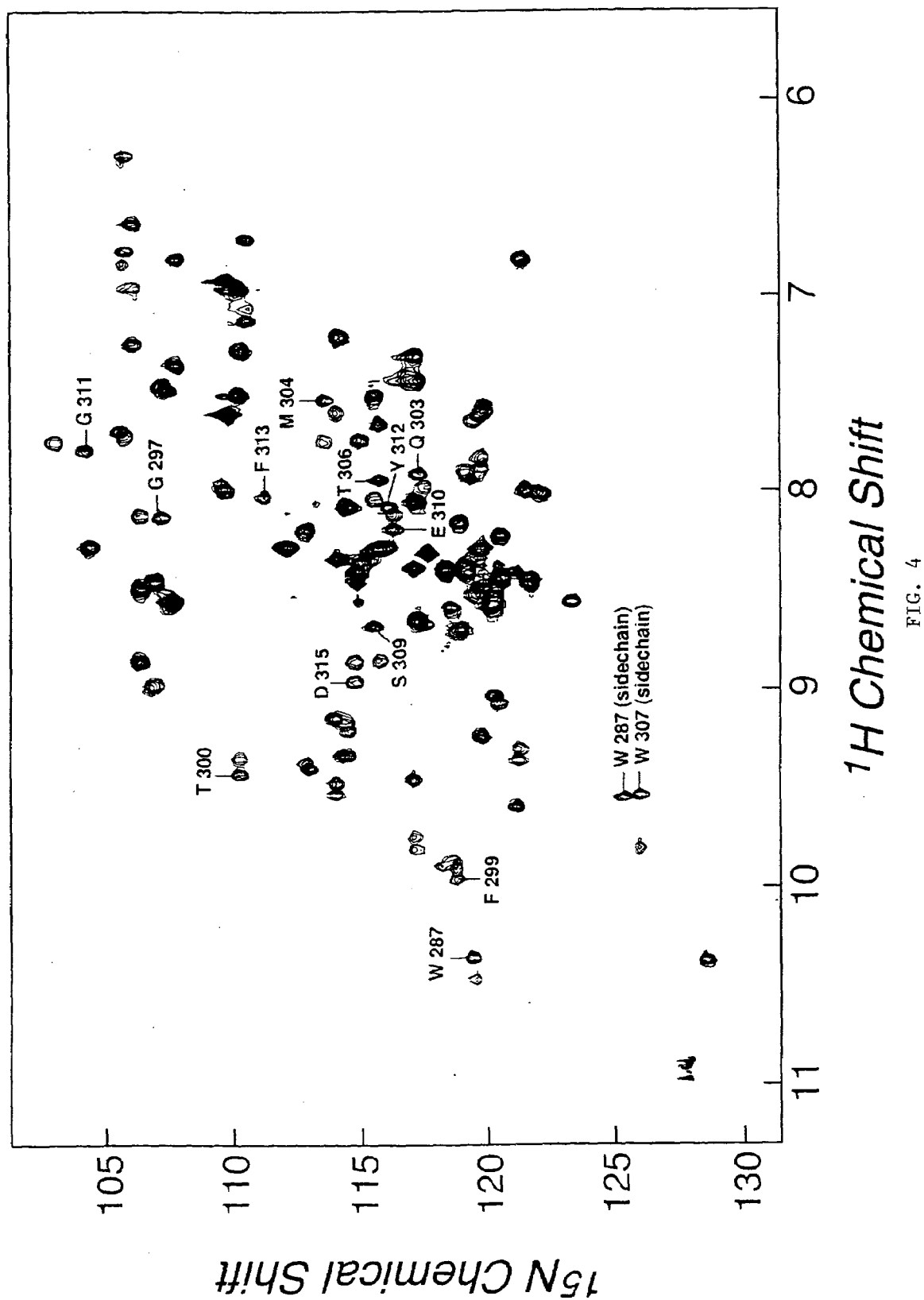
FIG. 4 is a color drawing showing HSQC spectra of the isolated and complexed CD2BP2 binding domain. The comparison shows that some NH resonances denoted by their sequence number in the uncomplexed spectrum (red) shift on the addition of equimolar amounts of a construct comprising a CD2-tail segment (amino acids 248–310 pf CD2) fused to GST (blue).

To further define the binding between CD2BP2 and the cytoplasmic tail of CD2 in vitro, NMR titration studies were performed. FIG. 4 shows the $^{15}$N—$^{1}$H correlation spectrum of the purified binding domain of CD2BP2 comprising amino acids 256–341 of the protein, where each NH group within the protein results in a signal in the NMR spectrum. The chemical shift dispersion is in agreement with a folded, native protein domain. Backbone resonance assignments were performed to define the in vitro binding at the level of individual amino acids. FIG. 4 also shows the $^{15}$N—$^{1}$H correlation spectrum of the CD2BP2 protein domain after the addition of equimolar amounts of a GST-fusion of the truncated CD2 tail (CD2$_{221-282}$). This truncated CD2 tail segment contains both PPPGHR (SEQ ID NO: 10) regions and showed full affinity in the yeast two-hybrid assay (FIG. 3B). Because the GST-CD2 tail fusion protein was not enriched isotopically with $^{15}$N, only the resonances arising from the CD2BP2 domain are seen in this spectrum. Compared with the unligated spectrum, certain of the resonances display significant chemical shift differences indicative of a binding event. This chemical shift difference indicates either that the respective residue directly participates in complex formation or is involved in a ligand-induced conformational change at a distance from the binding site. Because only a subset of residues show a significant chemical shift difference, it is most probable that this difference is caused by direct involvement in binding rather than a large conformational change of the protein. The latter would be expected to affect most of the residues within such a small protein domain. No chemical shift differences can be seen when the GST protein alone is used in the titration experiments. The latter result indicates that the truncated CD2 tail is responsible for the binding.

Resonances demonstrating chemical shift differences of >0.1 ppm ($^{1}$H) and >0.5 ppm ($^{15}$N) on binding are W287, G297, F299, Q303, M304, T306, W307, S309, G311, Y312, F313, and D315. Except for W287 and D315, each of these residues lies within the 17-amino acid segment suggested from the mutational studies to be essential for binding. The chemical shifts of the CD2BP2 cross peaks change in a manner dependent on the concentration of the ligand. This observation indicates that CD2BP2 is in fast exchange between free and bound forms, and, hence, the averaged signals are observed. Because there is no significant line broadening (<2 Hz) for proton signals that shift by ≈50 Hz, it is estimated that the off rates are faster than 1,000 s$^{-1}$ because the k$_{off}$ is $\pi\Delta^2/(4\,\delta\upsilon)$ for a two-site exchange where $\Delta$ is the chemical shift difference between the two states and $\delta\upsilon$ is the line broadening.

Figure 5A:
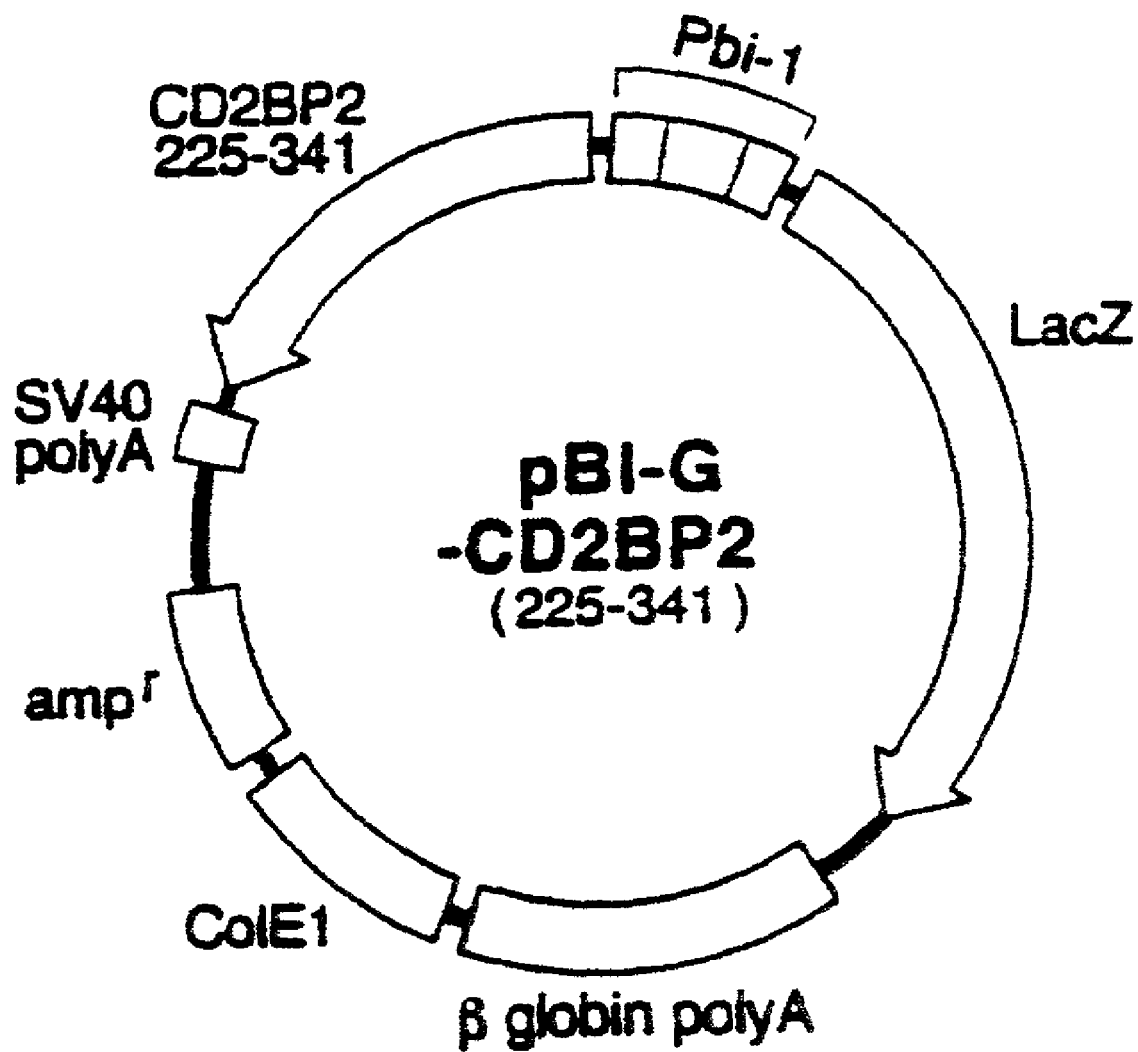
FIGS. 5A–5E show the regulation of CD2-stimulated T cell activation by CD2BP2. Shown is the effect of the expression of the CD2 binding segment (amino acids 225–34) of CD2BP2 on $Ca^{2-}$ influx and IL-2 production in Jurkat cells for CD2 crosslinking.
Figure 5B:
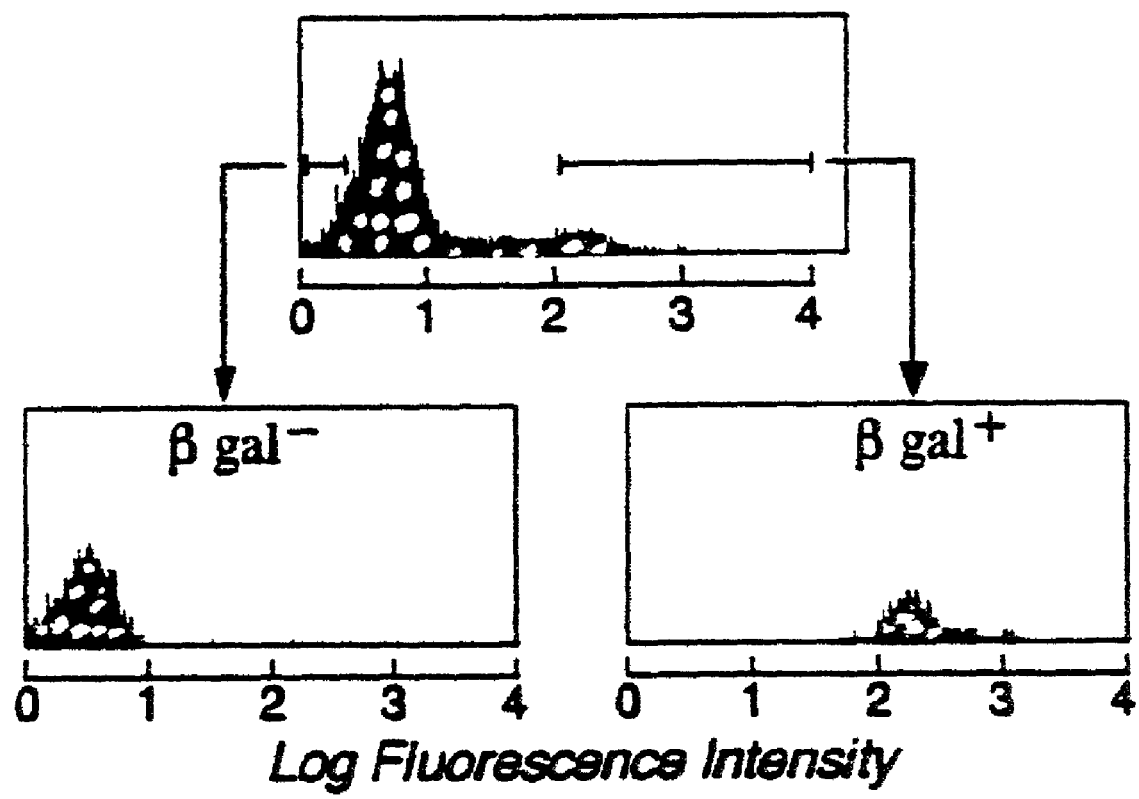
Figure 5C:
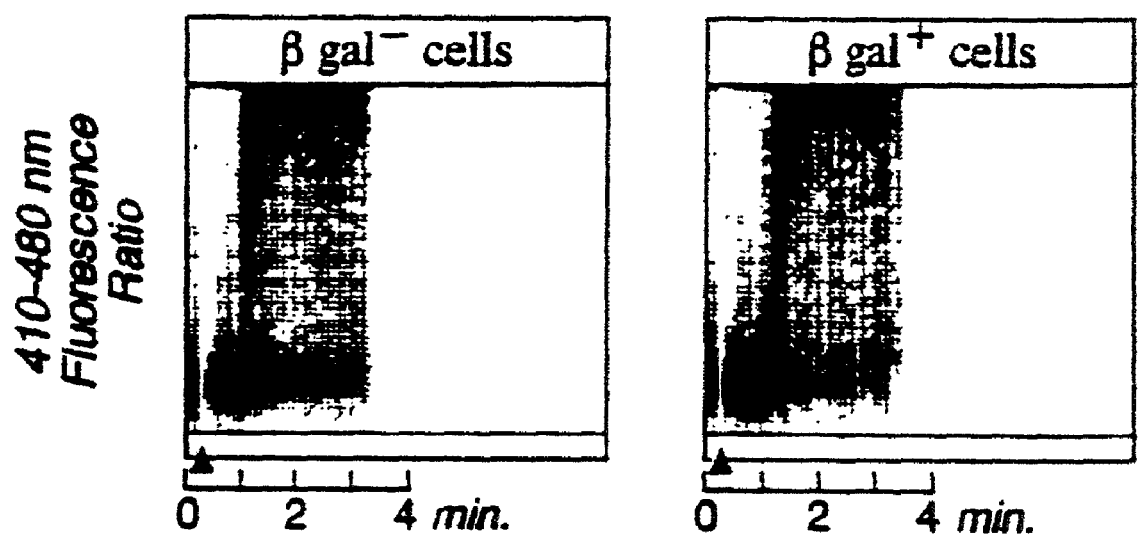
Figure 5D:
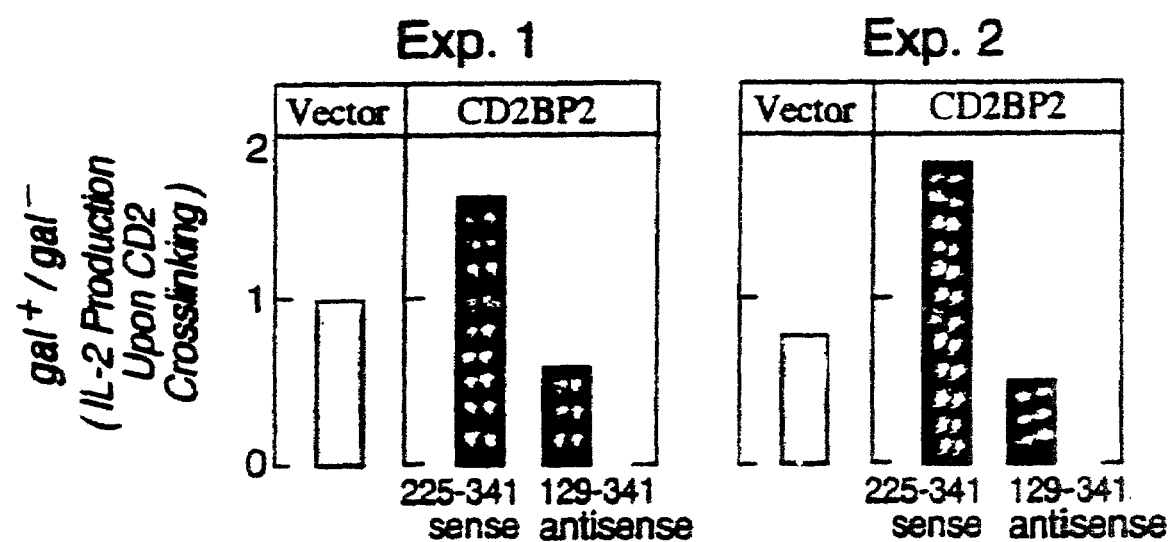
Figure 5E:
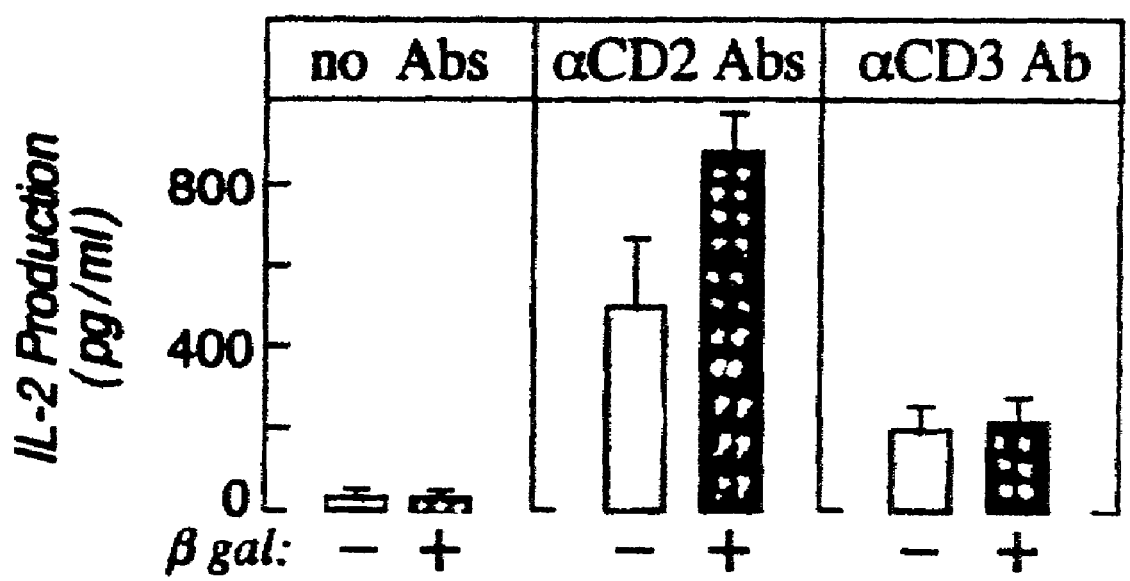

Next, the functional role of the CD2BP2 in T lymphocytes was investigated. To this end, a transient transfection assay was used in Jurkat cells by employing a reporter protein expression system based on a bidirectional promoter in combination with FACS-gal sorting as described (FIGS. 5A and B) (Nolan and Herzenberg, *Proc. Natl. Acad. Sci. USA* 85:2603–2607 (1998); Reem et al., *J. Immunol.* 139:130–134 (1987); Targan et al., *J. Immunol* 154:664–675 (1995); Ren et al., *Science* 259:1157–1161 (1993); Musacchio et al., *Prog. Biophys. Mol. Biol.* 61:283–297 (1994); Bork and Sudol, *Trends Biochem. Sci* 19:531–533 (1994)). Jurkat cells transfected with $CD2BP2_{225-341}$ were separated by FACS into plasmid-expressing and -nonexpressing subpopulations based on β-galactosidase (β-gal) activity and then were examined in functional assays. As shown in FIG. 5C, regardless of $CD2BP2_{225-341}$ (i.e., β-gal) expression, there was no difference in terms of $Ca^{2-}$ influx induced by CD2 crosslinking. However, although the pBI-G vector alone did not alter the CD2-triggered IL-2 production, the pBI-G-$CD2BP2_{225-341}^{sense}$ construct reproducibly enhanced IL-2 production 150–200%. By contrast, expression of the antisense strand decreased IL-2 production to ≈50% (FIG. 5D). To test whether CD2BP2 is also involved in T cell receptor-stimulated IL-2 production, additional experiments were performed in which transfected cells either were left unstimulated or were triggered by anti-CD2 or anti-CD3 mAbs. As shown in FIG. 5E, expression of CD2BP2 selectively enhances IL-2 production on CD2 crosslinking (clustering by a combination of anti-$T11_2$ plus anti-$T11_3$ mAbs). This selectivity of CD2BP2 for CD2-mediated activation is consistent with data showing differences in CD2 and CD3 signaling pathways (Gollob et al., *J. Exp. Med.* 182:721–731 (1995); Gollob et al., *J. Immunol.* 157:1886–1893 (1996); Semnani et al., *Scand J. Immunol.* 47:436–443 (1998); Sunder-Plassman and Reinherz, *J. Biol. Chem.* 273:24249–24257 (1998)).

The CD2BP2 molecule has several unique features that distinguish it from SH3 and WW domain-containing proteins. Although there is some difference in their detailed specificity, SH3 and WW domains both bind to PxxP-containing sequences. Consistent with this specificity, CD2-binding proteins with SH3 domains have been reported, and it has been determined that they mostly bind to the PPLP (SEQ ID NO: 11) sequence (amino acids 302–305 in FIG. 3B), which is an SH3 ligand consensus site (Bell et al., *J Exp. Med.* 183:169–178 (1997); Gassmann et al., *Eur. J. Immunol.* 24:139–144 (1994)) within the most highly conserved portion of the CD2 tail segment. In contrast, CD2BP2 binds to a site containing the two tandem PPPGHR (SEQ ID NO: 10) motifs but not to the SH3 ligand consensus sites (FIG. 3B). Moreover, unlike SH3 domains whose ligands require only eight residues for binding (Ren et al., *Science* 259:1157–1161(1993); Musacchio et al., *Prog. Biophys. Mol. Biol.* 61:283–297 (1994)), CD2BP2 requires a 21-residue segment. It is believed that this CD2BP2 binding segment transiently assumes a configuration necessary for interaction, perhaps regulated by divalent cations. Conservation of the dibasic residues within the two tandem motifs, including the histidine in human, mouse, rat, and horse CD2, is noteworthy. It has previously been shown that the PPPGHR (SEQ ID NO: 10)-containing region of the CD2 tail is essential for CD2 ectodomain-stimulated IL-2 production (Chang et al., *J. Exp. Med.* 169:2073–2083 (1989); Chang et al., *J. Exp. Med.* 172:351–355 (1990)). Although the mechanism by which the tandem PPPGHR (SEQ ID NO: 10) sequences trigger IL-2 gene activation on CD2 clustering is still unclear, it is possible that this region is needed for the proper orientation and/or function of the downstream SH3 ligand binding motif. Consistent with this notion, replacement of the dibasic HR residues of the PPPGHR (SEQ ID NO: 10) segment with DE residues weakens not only the binding of CD2BP2 to this region but also that of the SH3 domain of p59$^{fyn}$ to the downstream SH3 consensus site. Thus, it is believed that CD2BP2 may play a biologic role in coordinating the binding of other interactors to the more C-terminal region of the CD2 tail.

SH3 domains are made up of 5–6 antiparallel β-strands forming a compact, barrel-like structure. As shown by analysis of complexes of SH3 domains and their ligands, the ligand for a given SH3 domain forms a left-handed polyproline-type II helix whose interactions with the SH3 domain are mediated primarily by hydrophobic residues within the binding site (Ren et al., *Science* 259:1157–1161(1993); Musacchio et al., *Prog. Biophys. Mol. Biol.* 61:283–297 (1994)). WW domains form a three-stranded antiparallel β-strand with one of the two conserved tryptophan residues crucially involved in the interaction with the proline-rich ligand (Macias et al., *Nature* 382:646–649 (1996)). The in vivo binding assays described herein show that a number of aromatic residues of CD2BP2 probably are involved directly in the interaction with the proline-rich sequence motif of the CD2 cytoplasmic domain. However, structure-prediction methods and initial Nuclear Overhausen Effect (NOE) analysis indicate the presence of a central α-helix within the binding domain of CD2BP2 (residues 301–311). This helix is predicted to reside within the conserved 17-amino acid sequence shown herein to be necessary for the binding of the proline-rich ligand. It therefore appears that the binding domain of CD2BP2 defines a class of proline-rich recognition domains. In this fold, an α-helical rather than a β-strand structure displays those aromatic and hydrophobic residues necessary for the binding to the proline-rich ligand. Given that the CD2BP2 protein involved in binding to the PPPGHR (SEQ ID NO: 10) motif is expressed in different tissues, and that there is conservation of the GP[Y/F]xxxx [M/V]xxWxxxGYF (SEQ ID NO: 9) sequence in other unrelated proteins derived from different species, it is likely that this interaction is not restricted to lymphocytes, but rather represents a basis for protein-protein interaction.

Figure 6:
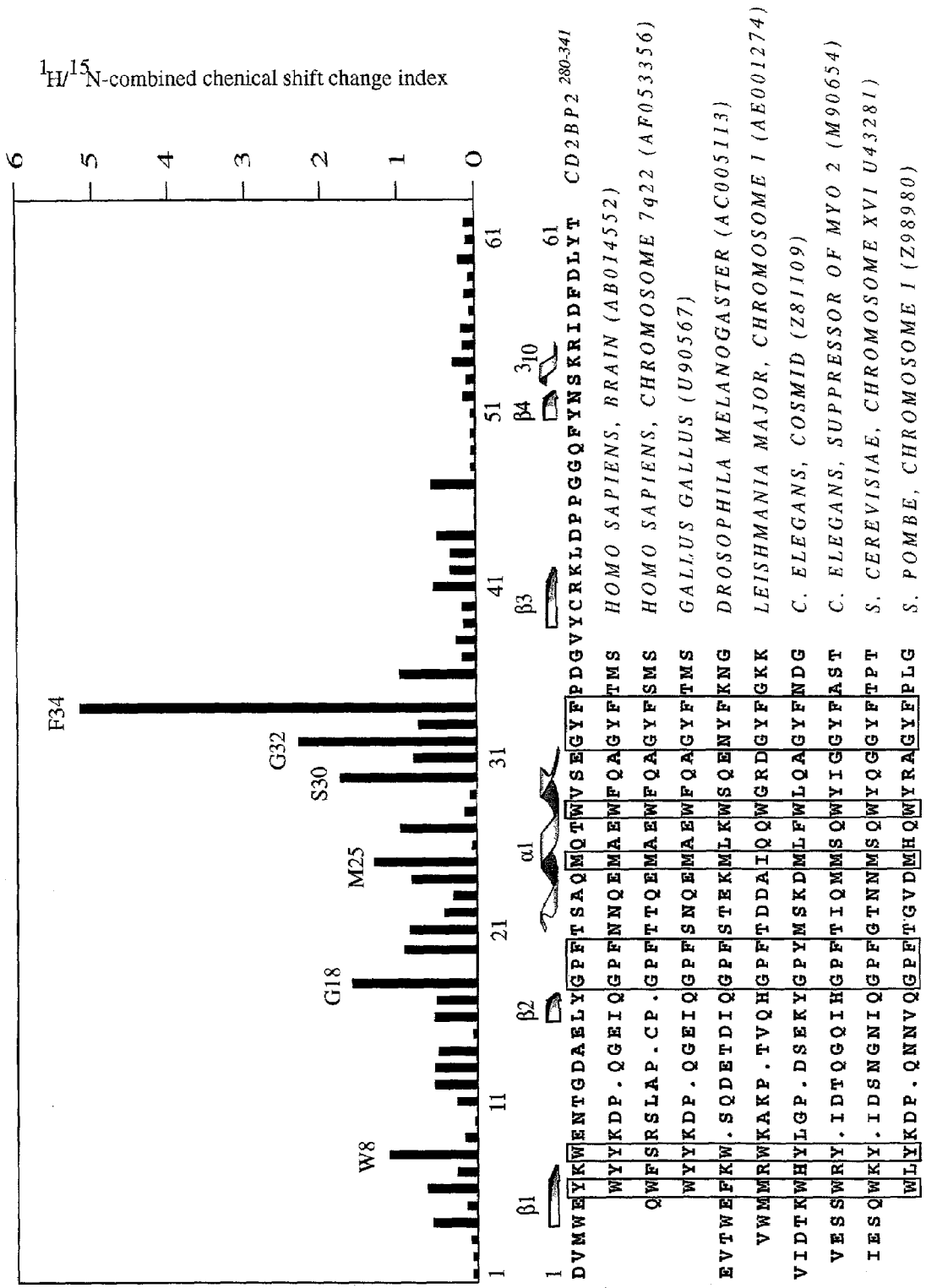
FIG. 6 shows the identification of a protein domain involved in binding a proline-rich ligand. The sequence of the CD2BP2 GYF domain (amino acids 1–62, corresponding to residues 280–341 of the CD2BP2 protein) is shown in comparison with hypothetical proteins from diverse species (lower panel). The homology region containing translated sequences were obtained by using a Ψ-Blast (Altschul, et al., *Nucleic Acids Res.* 25:3389–3402 (1997)) search. The accession number of the sequences shown are given in parenthesis. Boxed residues indicate conservation amongst species. For the CD2BP2 GYF domain the secondary structure elements as determined by NOE analysis of the NOESY-HSQC spectrum are plotted directly above the amino acid sequence. The backbone NH chemical shift differences between the unligated and ligated CD2BP2 GYF domain for each residue except for prolines are shown in the upper panel. The combined index of chemical shift change for $^{15}N$ and $^1H$ backbone atoms is determined by: $[(\Delta^1H\_cs)^2+(\Delta^{15}N\_cs)^2]^{1/2}$, where $\Delta^1H\_cs$ is in units of 0.1 ppm, and $\Delta^{15}N\_cs$ is in units of 0.5 ppm. The six residues with the highest chemical shift change index are labeled in the upper panel.

To define the structural basis for the interaction of this novel protein recognition module with the CD2 tail, the NMR structure of the C-terminal fragment of CD2BP2 (residues 256–341) was determined. Chemical shift and NOE analysis show that the first 24 residues of this fragment are unstructured, confining the proline-rich binding domain to the 62 C-terminal residues of CD2BP2. The sequence of this structurally defined domain is shown in FIG. 6 (lower panel), together with representative sequences from various eukaryotic species showing local homology to CD2BP2. Secondary structure analysis indicates an α/β-type fold, with a relatively high content of non-regular structure present (34 out of 62 residues). NMR binding experiments, in which increasing amounts of a GST-fusion protein containing the two PPPPGHR motifs of the CD2 tail were added to the $^{15}$N-labeled CD2BP2 binding domain, demonstrated the direct involvement of many of the conserved residues in the binding event. FIG. 6 (upper panel) provides a quantitative analysis of the $^{1}$H—$^{15}$N backbone chemical shift changes in the CD2BP2 binding domain upon addition of equimolar amounts of the proline-rich ligand for each amino acid residue. With the exception of W28 (the side-chain NH of which nevertheless becomes largely shifted) and P19 (which cannot be observed in this NMR experiment), there is a striking correlation between the extent of change in the chemical shift and the amino acid sequence conservation within the homology region. Hence, five out of the six residues with the largest change in chemical shift upon binding are highly conserved. In particular, the residues glycine 32, tyrosine 33 and phenylalanine 34 define a sequence stretch of high homology and the largest chemical shift perturbation upon binding are observed for G32 and F34. We therefore propose the proline-rich binding domain of CD2BP2 to be named GYF domain. Furthermore, since the conserved residues of the homology region of the CD2BP2 GYF domain (FIG. 6) are largely involved in the binding to the CD2 tail, we suggest a similar function for the other proteins containing the homology region, namely the recognition of proline-rich ligands.

Figure 7B:
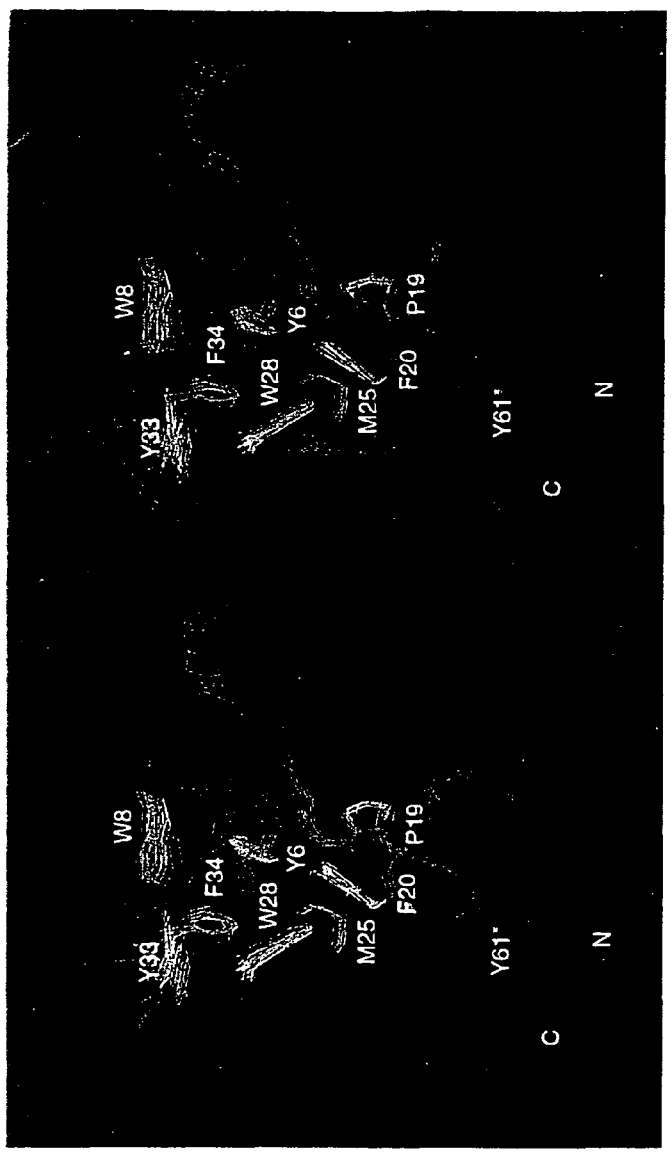
FIGS. 7A–7B show the NMR structure of the CD2BP2 GYF domain.
Figure 7A:
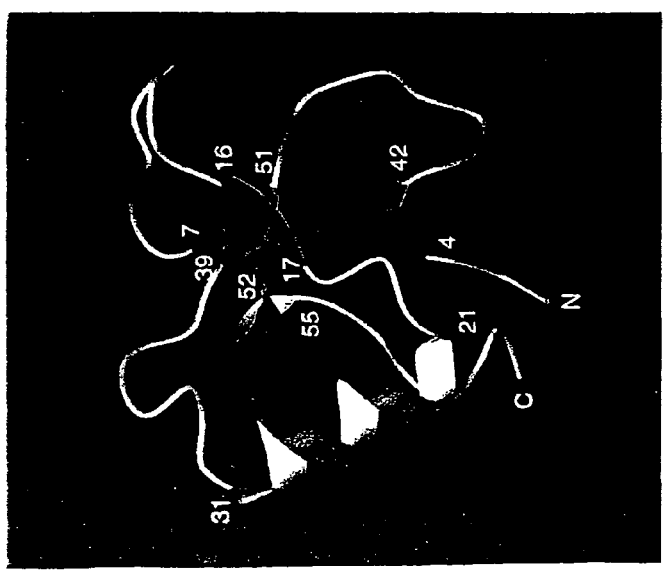

The fold of the GYF domain is depicted in FIG. 7A and reveals a compact domain, where an α-helix packs towards an antiparallel, twisted β-sheet in a β-β-α-β-β topology. The C-terminal end of the α-helix is tilted away from the β-sheet, allowing the aromatic side-chains of the bulge-forming GYF sequence to be placed in between the helix and the sheet. The outer two β-strands of the twisted β-sheet are extremely short. In the case of β-strand 2 this is due to a kink at positions G18 and P19, while Y51 is the only residue of β-strand 4 that displays a stable hydrogen bond pair with residue Y39 of the adjacent β-strand 3. One turn of a $3_{10}$-helix immediately follows β-strand 4 and the 6 C-terminal residues of the domain are close in space to the α-helix as well as to the N-terminal three residues. FIG. 7B shows an ensemble of 16 NMR structures, with secondary structure-elements color-coded as in FIG. 7A. All the side-chains of residues within the homology region with high sequence conservation (FIG. 6) are shown in yellow. Strikingly, this highlights the unique arrangement of the aromatic side-chains Y6, W8, F20, W28, Y33 and F34 within the GYF domain. These residues create a large hydrophobic surface and contribute to the core of the protein by making van der Waals interactions with M25, V38, Y39 and C40. This architecture of the GYF domain allows the molecule to form a compact fold with a relatively large binding surface. Mutational analysis (Nishizawa, et al., *Proc. Natl. Acad. Sci. USA* 95:14897–14902 (1998)) has shown that alanine substitutions of W28, G32, Y33 or F34 destroy the functional and/or structural integrity of the domain. G32 of the GYF motif allows the aromatic side-chain of Y33 to be placed adjacent to W28 and residue F34 to be central residue of the hydrophobic core. In addition, Y61, highlighted in green in FIG. 7, is a potential site for tyrosine phosphorylation (Nishizawa, et al., *Proc. Natl. Acad. Sci. USA* 95:14897–14902 (1998)). A tyrosine kinase can be envisaged to biochemically modify this site without affecting the binding of the GYF domain to the CD2 cytoplasmic domain.

Figure 8C:
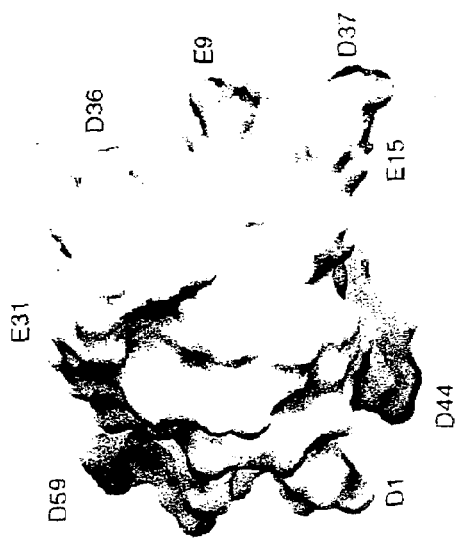
FIGS. 8A–8C show that the GYF domain ligand binding site is a contiguous surface containing many conserved hydrophobic residues. GRASP (Nicholls, et al., *Prot. Struct. Funct. Genet.* 11:282–293 (1991)) representations of the GYF domain with residues marked according to residue type and sequence number. Molecules are shown in the same orientation in the three representations.
Figure 8B:
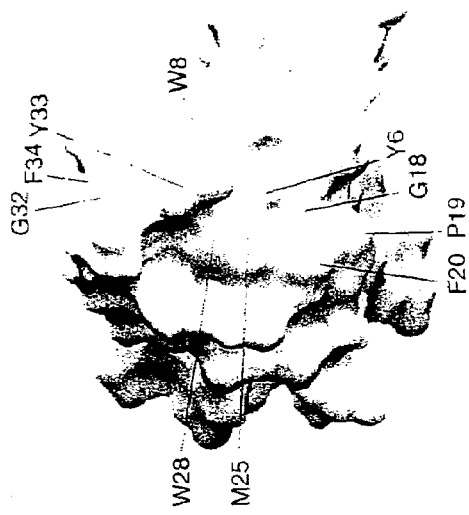
Figure 8A:
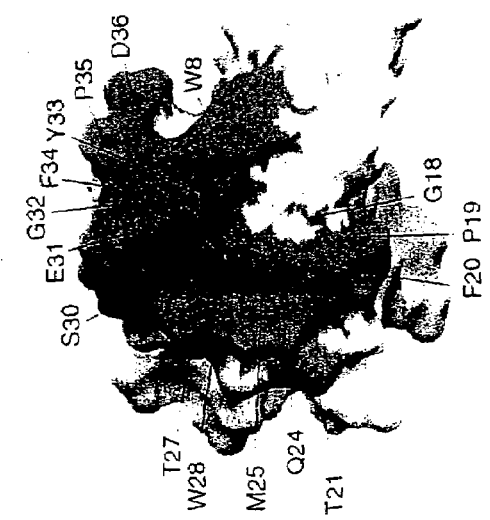

The CD2BP2 protein has been shown to bind specifically to a proline-rich stretch within the CD2 tail of the sequence PPPPGHRSQAPSHRPPPPGHR (SEQ ID NO: 22) (Nishizawa, et al., *Proc. Natl. Acad. Sci. USA* 95:14897–14902 (1998)). Deletion of either of the two proline-rich repeats abolishes binding in a yeast two-hybrid system. Moreover, mutation of either of the two HR dipeptide sequences neighboring the proline residues substantially decreases the affinity for CD2BP2 binding (Nishizawa, et al., *Proc. Natl. Acad. Sci. USA* 95:14897–14902 (1998)). Since this proline-rich stretch is not typical of SH3 or WW binding peptides (Pawson, *Nature* 373:573–580 (1995); Sudol, *Prog. Biophys. Mol. Biol.* 65:113–132 (1996)), it was speculated that the CD2BP2 protein displays unique features for the binding of its proline-rich ligand. FIG. 8A shows a GRASP (Nicholls, et al., *Prot. Struct. Funct. Genet.* 11:282–293 (1991)) representation of the GYF domain, with the binding surface, as mapped by the NMR experiment, colored in green. M25 and W28 of the α-helix form a continuous hydrophobic patch along with the $GPF_{18-20}$ and $GYF_{32-34}$ residues, as well as W8. Given that the side-chain of residue F34 of the GYF motif is largely buried in the protein core and yet F34 displays the largest chemical shift changes upon binding, it is likely that either a ligand-dependent structural rearrangement of the GYF loop-motif occurs, and/or there is a direct interaction of the NH group of F34 with the ligand, probably by forming a hydrogen bond. A number of binding surface residues displayed by the α-helix (T21, Q24, Q26, T27, S30) are polar, while E31 and D36 are the only charged residues of the binding site.

Close inspection of the ligand binding site of the CD2BP2 GYIF domain shows it to display a slightly bent, relatively smooth surface (FIG. 8A). A proline-rich ligand might be anticipated to bind along the axis defined by the α-helical residues of the binding site. Since four residues of the sequence PXXP (Pawson, *Nature* 373:573–580 (1995)) are able to adopt a proline-helical conformation, the PPPP (amino acids 1–4 or 15–18 of SEQ ID NO: 22) sequence of the PPPPGHR (amino acids 1–7 or 15–21 of SEQ ID NO: 22) repeat could assume such a conformation as well. FIG. 8B shows the surface area occupied by the conserved residues of the homology region of the GYF domain. Except for Y6, which is largely buried in the core of the protein, this area forms a subset of the contiguous surface of the whole binding site of the CD2BP2 GYF domain (FIGS. 8A and 8B in comparison). We suggest that the conserved hydrophobic patch defines the major binding surface interacting with proline-rich ligands. This is likely to be the case for CD2BP2 as well as for all the other proteins containing the homology region of the CD2BP2 GYF domain (FIG. 6). We speculate furthermore that, since only 6–8 residues can be placed along this hydrophobic patch, one of the two proline-rich repeats in the CD2 tail is primarily responsible for the binding to the conserved residues of the homology region. In agreement with this hypothesis, the arrangement of two tandem PPPPGHR (amino acids 1–7 or 15–21 of SEQ ID NO: 22) segments seems to be a peculiarity of the CD2 cytoplasmic domain, since a Ψ-BLAST sequence search (Altschul, et al., *Nucleic Acids Res.* 25:3389–3402 (1997)) revealed no significant homology to the PPPPGHRSQAPSHRPPPPGHR (SEQ ID NO: 22) sequence found in CD2. In addition, the distribution of charged residues within the homology region is different for each of the proteins compared in FIG. 6, implying that charged interactions might not be a conserved feature of the homology region containing proteins. In the case of the CD2BP2 GYF domain, however, E31 and D36 are part of the NMR mapped binding site and an number of additional negatively charged residues are located at the edge of the binding surface (FIG. 8C). No positive charge is present on this surface, suggesting that only acidic residues confer specificity to the interaction with the CD2 cytoplasmic domain, probably by interacting with the HR residues of the PPPPGHR (amino acids 1–7 or 15–21 of SEQ ID NO: 22) sequence.

The fold of the GYP domain is unrelated to the structures of SH3 (Musacchio, et al., *Nature* 359:851–855 (1992); Yu, et al., *Science* 258:1665–1668 (1992)) or WW (Macias, et al., *Nature* 382:646–649 (1996)) domains, which display the side-chains for the interaction with the proline-rich ligand by means of β-strands and β-strand connecting loops. Nonetheless, there are some features shared between all three protein modules. For example, conserved hydrophobic residues line up to create a contiguous surface stretch. These residues define the axis for the binding of the proline-rich ligand in the case of SH3 and WW domains and we suggest this to be the case for the GYF domain as well. Second, glutamine or asparagine side-chains within SH3 and WW domains contribute to the interaction with the respective peptides by the potential formation of hydrogen bonds (Macias, et al., *Nature* 382:646–649 (1996); Musacchio, et al., *Prog. Biophys. Mol. Biol.* 61:283–297 (1994)). In the case of the GYP domain the side-chain amide protons of Q48 become largely shifted upon addition of the proline-rich ligand (Nishizawa, et al., *Proc. Natl. Acad. Sci. USA* 95:14897–14902 (1998)), indicating a direct interaction with the ligand. Third, a specificity pocket within SH3 and WW domains interacts with non-proline residues of the ligand, restricting the promiscuity of these domains. The surface properties and charge distribution of the GYP domain binding site also argues for the necessity of non-proline residues to be present in the ligand for an optimal interaction. Residues E31 and Y33 extrude significantly from the surface, creating a wall at the C-terminal end of the α-helix. In order to interact with residues of the a-helix as well as the site defined by W8 and its spatially adjacent residues, one or more non-proline residues probably have to allow the ligand to bent around these extruding side-chains. The presence of a glycine residue within the PPPPGHR (amino acids 1–7 or 15–21 of SEQ ID NO: 22)-recognition motifs could provide this conformational flexibility within the ligand. Finally, the N and C-terminus of all three domains are close in space. This facilitates the ability of 5H3 and WW domains to function as universal protein-protein interaction modules present in many proteins involved in signal transduction. A similar adapter function might be anticipated for the GYF domain.

The function of a second proline-rich stretch within the ligand recognition motif of the CD2 cytoplasmic tail may either contribute directly to CD2BP2 binding or, alternatively, aid in the binding of the first proline-rich sequence stretch by adding stability to a conformation of the CD2 cytoplasmic domain favorable for the binding to the GYF domain. In this respect it is noteworthy that there are several species-conserved histidine residues (H242, H264, H278, H297 in human CD2) present in the cytoplasmic domain of CD2, which might form a putative zinc binding site. In vitro co-immunoprecipitation assays indicate a greater amount of the CD2BP2 GYF domain bound to the recognition motif of the CD2 tail on GST-CD2 beads in the presence of $ZnCl_2$ (data not shown). The two conserved histidines of the recognition motif (H264 and H278) might therefore be part of a metal induced conformation. The presence of metal ions was shown to be important for the binding of the unrelated CD2BP 1 protein to the CD2 tail (Li, et al., *Embo J.* 17:7320–7336 (1998)) and it has long been known that T cell activation via CD2 gives rise to a large influx of extracellular calcium (Alcover, et al., *Proc. Natl. Acad. Sci. USA* 83:2614–2618 (1986)). Albeit the specificity of the CD2 cytoplasmic domain for different metal ions remains to be investigated, it is likely that metal coordination might provide a mechanism for more distant sequence stretches of the CD2 tail to come close in space and allow different CD2 tail binding proteins to interact. This hypothesis is in agreement with earlier findings that binding of the tyrosine kinase p59$^{fyn}$ to the C-terminal proline-stretch of the CD2 tail is attenuated by mutations of the HR sequences within either of the two N-terminal PPPPGHR proline segments (Nishizawa, et al., *Proc. Natl. Acad. Sci. USA* 95:14897–14902 (1998)).

Aside from providing insight into CD2-based signaling processes, the current findings will serve as impetus for investigating the role of other GYF domain containing proteins. It is predicted that these additional GYF domains identified by homology search (for example in FIG. 6) have a similar overall fold as the one found for CD2BP2. A dominant α-helix and its adjacent loops will create a hydrophobic patch along the respective surfaces, capable of binding proline-rich sequences. Whether the proline-rich ligands of the GYF domains will be required to obey the rules found to be common for the SH3 and WW domain ligands (Nguyen, et al., *Science* 282:2088–2092 (1998)), will be revealed by the comparison of the three-dimensional structure of different GYF domain/ligand complexes.

Thus, the invention pertains to isolated nucleic acid molecules described herein. In one embodiment, a nucleic acid molecule of the invention comprises a nucleotide sequence selected of SEQ ID NO: 1 or the complement of SEQ ID NO: 1. In another embodiment, the nucleic acid molecule hybridizes under high stringency conditions to the nucleotide sequence of SEQ ID NO: 1 or the complement of SEQ ID NO: 1. In a further embodiment, the nucleic acid molecule of the invention comprises a nucleotide sequence which is greater than about 80 percent, preferably greater than about 85 percent, more preferably greater than about 90 percent, and even more preferably greater than about 95 percent, identical to the nucleotide sequence of SEQ ID NO: 1 or the complement of SEQ ID NO: 1.

The invention also relates to an isolated nucleic acid molecule consisting essentially of a nucleotide sequence of SEQ ID NO: 1 or the complement of SEQ ID NO: 1. The invention further relates to an isolated portion of SEQ ID NO: 1 or the complement of SEQ ID NO: 1, which portion is sufficient in length to distinctly characterize the sequence. For example, the isolated portion can be from about 7 to about 15 nucleotides in length (e.g., about 10 nucleotides in length) and more preferably from about 15 to about 25 nucleotides in length. Particularly useful portions include, but are not limited to, nucleotides encoding amino acids 129–341 of CD2BP2, nucleotides encoding amino acids 225–341 of CD2BP2, nucleotides encoding amino acids 256–341 of CDBP2, nucleotides encoding amino acids 256–338 of CDBP2, nucleotides encoding amino acids 297–313 of CDBP2, and nucleotides encoding amino acids 291–317 of CDBP2, as well as nucleotides encoding amino acids 260–265 of CD2, and nucleotides encoding amino acids 274–279 of CD2, and the complements of these nucleotide sequences. The nucleotide sequences encoding these peptide regions can be naturally-occurring (e.g., the nucleotide sequences shown in FIG. 1A and FIG. 3B) or can be non-naturally occurring. Such portions or fragments are useful, for example, as probes, e.g., for diagnostic methods, and also as primers. Particularly preferred primers and probes selectively hybridize to nucleic acid molecules comprising the nucleotide sequence of SEQ ID NO: 1 or the complement of SEQ ID NO: 1. For example, fragments which encode antigenic proteins or polypeptides described herein are useful.

As appropriate, nucleic acid molecules of the present invention can be RNA, for example, mRNA, or DNA, such as cDNA and genomic DNA. DNA molecules can be double-stranded or single-stranded; single stranded RNA or DNA can be either the coding, or sense, strand or the non-coding, or antisense, strand. Preferably, the nucleic acid molecule comprises at least about 6 nucleotides, more preferably at least about 10 nucleotides, more preferably at least about 50 nucleotides, and even more preferably at least about 200 nucleotides. The nucleic acid molecule can include all or a portion of the coding sequence of the CD2BP2 gene and can further comprise additional non-coding sequences such as introns and non-coding 3' and 5' sequences (including regulatory sequences, for example). Additionally, the nucleic acid molecule can be fused to a marker sequence, for example, a sequence which encodes a polypeptide to assist in isolation or purification of the polypeptide. Such sequences include, but are not limited to, those which encode a glutathione-S-transferase (GST) fusion protein and those which encode a hemaglutin A (HA) polypeptide marker from influenza.

As used herein, an "isolated" gene or nucleic acid molecule is intended to mean a gene or nucleic acid molecule which is not flanked by nucleic acid molecules which normally (in nature) flank the gene or nucleic acid molecule and/or has been completely or partially purified from other transcribed sequences (as in a cDNA or RNA library). For example, an isolated nucleic acid of the invention may be substantially isolated with respect to the complex cellular milieu in which it naturally occurs. In some instances, the isolated material will form part of a composition (for example, a crude extract containing other substances), buffer system or reagent mix. In other circumstance, the material may be purified to essential homogeneity, for example as determined by PAGE or column chromatography such as HPLC. Preferably, an isolated nucleic acid comprises at least about 50, 80 or 90 percent (on a molar basis) of all macromolecular species present. Thus, an isolated gene or nucleic acid molecule can include a gene or nucleic acid molecule which is synthesized chemically or by recombinant means. Thus, recombinant DNA contained in a vector are included in the definition of "isolated" as used herein. Also, isolated nucleic acid molecules include recombinant DNA molecules in heterologous host cells, as well as partially or substantially purified DNA molecules in solution. In vivo and in vitro RNA transcripts of the DNA molecules of the present invention are also encompassed by "isolated" nucleic acid molecules. Such isolated nucleic acid molecules are useful in the manufacture of the encoded protein, as probes for isolating homologous sequences (e.g., from other mammalian species), for gene mapping (e.g., by in situ hybridization with chromosomes), or for detecting expression of the gene in tissue (e.g., a tissue biopsy or blood sample) such as by Northern blot analysis.

The invention also pertains to nucleic acid molecules which hybridize under high stringency hybridization conditions (e.g., for selective hybridization) to a nucleotide sequence described herein. Hybridization probes are oligonucleotides which bind in a base-specific manner to a complementary strand of nucleic acid. Suitable probes include polypeptide nucleic acids, as described in (Nielsen et al., *Science* 254, 1497–1500 (1991)).

Such nucleic acid molecules can be detected and/or isolated by specific hybridization (e.g., under high stringency conditions). "Stringency conditions" for hybridization is a term of art which refers to the incubation and wash conditions, e.g., conditions of temperature and buffer concentration, which permit hybridization of a particular nucleic acid to a second nucleic acid; the first nucleic acid may be perfectly (i.e., 100%) complementary to the second, or the first and second may share some degree of complementarity which is less than perfect (e.g., 60%, 75%, 85%, 95%). For example, certain high stringency conditions can be used which distinguish perfectly complementary nucleic acids from those of less complementarity.

"High stringency conditions", "moderate stringency conditions" and "low stringency conditions" for nucleic acid hybridizations are explained on pages 2.10.1–2.10.16 and pages 6.3.1–6 in *Current Protocols in Molecular Biology* (Ausubel, F. M. et al., "*Current Protocols in Molecular Biology*", John Wiley & Sons, (1998)) the teachings of which are hereby incorporated by reference. The exact conditions which determine the stringency of hybridization depend not only on ionic strength (e.g., 0.2×SSC, 0.1×SSC), temperature (e.g., room temperature, 42° C., 68° C.) and the concentration of destabilizing agents such as formamide or denaturing agents such as SDS, but also on factors such as the length of the nucleic acid sequence, base composition, percent mismatch between hybridizing sequences and the frequency of occurrence of subsets of that sequence within other non-identical sequences. Thus, high, moderate or low stringency conditions can be determined empirically.

By varying hybridization conditions from a level of stringency at which no hybridization occurs to a level at which hybridization is first observed, conditions which will allow a given sequence to hybridize (e.g., selectively) with the most similar sequences in the sample can be determined.

Exemplary conditions are described in Krause, M. H. and S. A. Aaronson, *Methods in Enzymology*, 200:546–556 (1991). Also, in, Ausubel, et al., "*Current Protocols in Molecular Biology*", John Wiley & Sons, (1998), which describes the determination of washing conditions for moderate or low stringency conditions. Washing is the step in which conditions are usually set so as to determine a minimum level of complementarity of the hybrids. Generally, starting from the lowest temperature at which only homologous hybridization occurs, each ° C. by which the final wash temperature is reduced (holding SSC concentration constant) allows an increase by 1% in the maximum extent of mismatching among the sequences that hybridize. Generally, doubling the concentration of SSC results in an increase in $T_m$ of ~17° C. Using these guidelines, the washing temperature can be determined empirically for high, moderate or low stringency, depending on the level of mismatch sought.

For example, a low stringency wash can comprise washing in a solution containing 0.2×SSC/0.1% SDS for 10 min at room temperature; a moderate stringency wash can comprise washing in a prewarmed solution (42° C.) solution containing 0.2×SSC/0.1% SDS for 15 min at 42° C.; and a high stringency wash can comprise washing in prewarmed (68° C.) solution containing 0.1×SSC/0.1% SDS for 15 min at 68° C. Furthermore, washes can be performed repeatedly or sequentially to obtain a desired result as known in the art.

Equivalent conditions can be determined by varying one or more of the parameters given as an example, as known in the art, while maintaining a similar degree of identity or similarity between the target nucleic acid molecule and the primer or probe used. Hybridizable nucleic acid molecules are useful as probes and primers, e.g., for diagnostic applications.

As used herein, the term "primer" refers to a single-stranded oligonucleotide which acts as a point of initiation of template-directed DNA synthesis under appropriate conditions (e.g., in the presence of four different nucleoside triphosphates and an agent for polymerization, such as, DNA or RNA polymerase or reverse transcriptase) in an appropriate buffer and at a suitable temperature. The appropriate length of a primer depends on the intended use of the primer, but typically ranges from 15 to 30 nucleotides. Short primer molecules generally require cooler temperatures to form sufficiently stable hybrid complexes with the template. A primer need not reflect the exact sequence of the template, but must be sufficiently complementary to hybridize with a template. The term "primer site" refers to the area of the target DNA to which a primer hybridizes. The term "primer pair" refers to a set of primers including a 5' (upstream) primer that hybridizes with the 5' end of the DNA sequence to be amplified and a 3' (downstream) primer that hybridizes with the complement of the 3' end of the sequence to be amplified.

The invention also pertains to nucleic acid molecules which have a substantial identity with the nucleic acid molecules described herein; particularly preferred are nucleic acid molecules which have at least about 80 percent, preferably at least about 85 percent, more preferably at least about 90 percent, and even more preferably at least about 95 percent, identity with nucleic acid molecules described herein.

To determine the percent identity of two nucleotide sequences, the sequences are aligned for optimal comparison purposes (e.g., gaps can be introduced in the sequence of a first nucleotide sequence). The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences (i.e., % identity=# of identical positions/total # of positions×100).

The determination of percent identity between two sequences can be accomplished using a mathematical algorithm. A preferred, non-limiting example of a mathematical algorithm utilized for the comparison of two sequences is the algorithm of Karlin et al., *Proc. Natl. Acad. Sci. USA*, 90:5873–5877 (1993). Such an algorithm is incorporated into the NBLAST program which can be used to identify sequences having the desired identity to nucleotide sequences of the invention. To obtain gapped alignments for comparison purposes, Gapped BLAST can be utilized as described in Altschul et al., *Nucleic Acids Res*, 25:3389–3402 (1997). When utilizing BLAST and Gapped BLAST programs, the default parameters of the respective programs (e.g., NBLAST) can be used. In one embodiment, parameters for sequence comparison can be set at W=12. Parameters can also be varied (e.g., W=5 or W=20). The value "W" determines how many continuous nucleotides must be identical for the program to identify two sequences as containing regions of identity.

Thus, nucleic acid molecules which comprise a nucleotide sequence which is different from the naturally-occurring nucleic acid molecule but which, due to the degeneracy of the genetic code, encode the same protein or polypeptide are the subject of this invention. The invention also encompasses variations of the nucleic acid molecules of the invention, such as those encoding portions, analogues or derivatives of the encoded protein or polypeptide. Such variations can be naturally-occurring, such as in the case of allelic variation, or non-naturally-occurring, such as those induced by various mutagens and mutagenic processes. Intended variations include, but are not limited to, addition, deletion and substitution of one or more nucleotides which can result in conservative or non-conservative amino acid changes, including additions and deletions. Preferably, the nucleotide or amino acid variations are silent; that is, they do not alter the characteristics or activity of the encoded protein or polypeptide. As used herein, activities of the encoded protein or polypeptide include, but are not limited to, catalytic activity, binding function, antigenic function and oligomerization function.

Nucleotide sequences of the invention can be used to express recombinant protein for analysis, characterization or diagnostic or therapeutic use, or as markers for tissues in which the corresponding protein is expressed constitutively, during tissue differentiation, or in diseased states. The nucleic acid sequences can also be used as molecular weight markers on Southern gels, and as chromosome markers which are labelled to map related gene positions. The nucleic acid sequences can also be compared with endogenous DNA sequences in patients to identify genetic disorders, and as probes, such as to hybridize and discover related DNA sequences or to subtract out known sequences from a sample. The nucleic acid sequences can further be used to derive primers for genetic fingerprinting, to raise anti-protein antibodies using DNA immunization techniques, and as an antigen to raise anti-DNA antibodies or elicit immune responses.

The nucleotide sequences of the nucleic acid molecules described herein, e.g., SEQ ID NO: 1 and the complement of SEQ ID NO: 1, can be amplified by methods known in the art. For example, this can be accomplished by e.g., PCR. See generally *PCR Technology: Principles and Applications for DNA Amplification* (ed. H. A. Erlich, Freeman Press, NY, N.Y., 1992); *PCR Protocols: A Guide to Methods and Applications* (eds. Innis, et al., Academic Press, San Diego, Calif., 1990); Mattila et al., *Nucleic Acids Res.* 19, 4967 (1991); Eckert et al., *PCR Methods and Applications* 1, 17 (1991); *PCR* (eds. McPherson et al., IRL Press, Oxford); and U.S. Pat. No. 4,683,202.

Other suitable amplification methods include the ligase chain reaction (LCR) (see Wu and Wallace, *Genomics* 4, 560 (1989), Landegren et al., *Science* 241, 1077 (1988), transcription amplification (Kwoh et al., *Proc. Natl. Acad. Sci. USA* 86, 1173 (1989)), and self-sustained sequence replication (Guatelli et al., *Proc. Nat. Acad. Sci. USA*, 87, 1874 (1990)) and nucleic acid based sequence amplification (NASBA). The latter two amplification methods involve isothermal reactions based on isothermal transcription, which produce both single stranded RNA (ssRNA) and double stranded DNA (dsDNA) as the amplification products in a ratio of about 30 or 100 to 1, respectively.

The amplified DNA can be radiolabelled and used as a probe for screening a cDNA library mRNA in λzap express, ZIPLOX or other suitable vector to identify homologous nucleotide sequences. Corresponding clones can be isolated, DNA can be obtained following in vivo excision, and the cloned insert can be sequenced in either or both orientations by art recognized methods, to identify the correct reading frame encoding a protein of the appropriate molecular weight. For example, the direct analysis of the nucleotide sequence of homologous nucleic acid molecules of the present invention can be accomplished using either the dideoxy chain termination method or the Maxam Gilbert method (see Sambrook et al., *Molecular Cloning, A Laboratory Manual* (2nd Ed., CSHP, New York 1989); Zyskind et al., *Recombinant DNA Laboratory Manual*, (Acad. Press, 1988)). Using these or similar methods, the protein(s) and the DNA encoding the protein can be isolated, sequenced and further characterized.

With respect to protein or polypeptide identification, bands identified by gel analysis can be isolated and purified by HPLC, and the resulting purified protein can be sequenced. Alternatively, the purified protein can be enzymatically digested by methods known in the art to produce polypeptide fragments which can be sequenced. The sequencing can be performed, for example, by the methods of Wilm et al. (*Nature* 379(6564):466–469 (1996)). The protein may be isolated by conventional means of protein biochemistry and purification to obtain a substantially pure product, i.e., 80, 95 or 99% free of cell component contaminants, as described in Jacoby, *Methods in Enzymology* Volume 104, Academic Press, New York (1984); Scopes, *Protein Purification, Principles and Practice,* 2nd Edition, Springer-Verlag, N.Y. (1987); and Deutscher (ed), *Guide to Protein Purification, Methods in Enzymology*, Vol. 182 (1990). If the protein is secreted, it can be isolated from the supernatant in which the host cell is grown. If not secreted, the protein can be isolated from a lysate of the host cells.

In addition to substantially full-length CD2BP2 polypeptides encoded by nucleic acid molecules described herein, the present invention includes biologically active fragments of the polypeptides, or analogs thereof, including organic molecules which simulate the interactions of the polypeptides. Biologically active fragments include any portion of the full-length polypeptide which confers a biological function on the variant gene product, including ligand (e.g., CD2) binding and antibody binding.

This invention also pertains to an isolated protein or polypeptide encoded by the nucleic acid molecules of the invention. The encoded proteins or polypeptides of the invention can be partially or substantially purified (e.g., purified to homogeneity), and/or are substantially free of other proteins. According to the invention, the amino acid sequence of the polypeptide can be that of the naturally-occurring protein (e.g., SEQ ID NO: 2) or can comprise alterations therein. Such alterations include conservative or non-conservative amino acid substitutions, additions and deletions of one or more amino acids; however, such alterations should preserve at least one activity of the encoded protein or polypeptide, i.e., the altered or mutant protein should be an active derivative of the naturally-occurring protein. For example, the mutation(s) can preferably preserve the three dimensional configuration of the binding and/or catalytic site of the native protein. The presence or absence of biological activity or activities (e.g., CD2 binding, alteration of calcium flux or IL-2 production) can be determined by various functional assays as described herein and known in the art. Moreover, amino acids which are essential for the function of the encoded protein or polypeptide can be identified by methods known in the art. Particularly useful methods include identification of conserved amino acids in the family or subfamily, site-directed mutagenesis and alanine-scanning mutagenesis (for example, Cunningham and Wells, *Science* 244:1081–1085 (1989)), crystallization and nuclear magnetic resonance. For example, particular residues in both CD2 and CD2BP2 have been identified herein as being essential to the binding of CD2BP2 to CD2, and these residues would not be suitable for alteration if retention of binding characteristics are desired. The altered polypeptides produced by these methods can be tested for particular biologic activities, including binding to ligand (e.g., CD2) immunogenicity and antigenicity.

Specifically, appropriate amino acid alterations can be made on the basis of several criteria, including hydrophobicity, basic or acidic character, charge, polarity, size, the presence or absence of a functional group (e.g., —SH or a glycosylation site), and aromatic character. Assignment of various amino acids to similar groups based on the properties above will be readily apparent to the skilled artisan; further appropriate amino acid changes can also be found in Bowie et al. (*Science* 247:1306–1310(1990)).

For example, conservative amino acid replacements can be those that take place within a family of amino acids that are related in their side chains. Genetically encoded amino acids are generally divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cystine, serine, threonine, tyrosine. Phenylalanine, tryptophan and tyrosine are sometimes classified jointly as aromatic amino acids. For example, it is reasonable to expect that an isolated replacement of a leucine with an isoleucine or valine, an aspartate with a glutamate, a threonine with a serine or a similar conservative replacement of an amino acid with a structurally related amino acid will not have a major effect on activity or functionality.

The encoded polypeptide can also be a fusion protein comprising all or a portion of the amino acid sequence fused to an additional component, with optional linker sequences. Additional components, such as radioisotopes and antigenic tags, can be selected to assist in the isolation or purification of the polypeptide or to extend the half life of the polypeptide; for example, a hexahistidine tag would permit ready purification by nickel chromatography. The fusion protein can contain, e.g., a glutathione-S-transferase (GST), thioredoxin (TRX) or maltose binding protein (MBP) component to facilitate purification; kits for expression and purification of such fusion proteins are commercially available. The polypeptides of the invention can also be tagged with an epitope and subsequently purified using antibody specific to the epitope using art recognized methods. Additionally, all or a portion of the polypeptide can be fused to carrier molecules, such as immunoglobulins, for many purposes, including increasing the valency of protein binding sites. For example, the polypeptide or a portion thereof can be linked to the Fc portion of an immunoglobulin; for example, such a fusion could be to the Fc portion of an IgG molecule to create a bivalent form of the protein. Furthermore, polypeptides of the present invention can be progenitors of the active protein; progenitors are molecules which are cleaved to form an active molecule.

Polypeptides described herein can be isolated from naturally-occurring sources, chemically synthesized or recombinantly produced. Synthetically-constructed polypeptides, by virtue of sharing primary, secondary or tertiary structural and/or conformational characteristics with the native polypeptide, may possess biological properties in common with the native polypeptide, such as biological activity and immunological cross-reaction. Polypeptides or proteins of the present invention can be used as a molecular weight marker on SDS-PAGE gels or on molecular sieve gel filtration columns using art-recognized methods. Polypeptides of the invention can also be expressed as a product of transgenic animals, e.g., as a component of the milk of transgenic cows, goats, pigs or sheep having somatic or germ cells containing a nucleotide sequence encoding the polypeptide.

The polypeptides of the present invention can be used to raise antibodies or to elicit an immune response. The polypeptides can also be used as a reagent, e.g., a labelled reagent, in assays to quantitatively determine levels of the protein or a molecule to which it binds (e.g., a receptor or a ligand) in biological fluids. The polypeptides can also be used as markers for tissues in which the corresponding protein is preferentially expressed, either constitutively, during tissue differentiation, or in a diseased state. The polypeptides can be used to isolated a corresponding binding partner, e.g., receptor or ligand, such as, for example, in an interaction trap assay, and to screen for peptide or small molecule antagonists or agonists of the binding interaction.

The invention also provides expression vectors containing a nucleic acid sequence described herein, operably (operatively) linked to at least one regulatory sequence. Many such vectors are commercially available, and other suitable vectors can be readily prepared by the skilled artisan. "Operably linked" or "operatively linked" is intended to meant that the nucleic acid molecule is linked to a regulatory sequence in a manner which allows expression of the nucleic acid sequence. Regulatory sequences are art-recognized and are selected to produce the encoded polypeptide or protein. Accordingly, the term "regulatory sequence" includes promoters, enhancers, and other expression control elements which are described in Goeddel, *Gene Expression Technology: Methods in Enzymology* 185, Academic Press, San Diego, Calif. (1990). For example, the native regulatory sequences or regulatory sequences native to the transformed host cell can be employed. It should be understood that the design of the expression vector may depend on such factors as the choice of the host cell to be transformed and/or the type of protein desired to be expressed. For instance, the polypeptides of the present invention can be produced by ligating the cloned gene, or a portion thereof, into a vector suitable for expression in either prokaryotic cells, eukaryotic cells or both (see, for example, Broach, et al., *Experimental Manipulation of Gene Expression*, ed. M. Inouye (Academic Press, 1983) p. 83; *Molecular Cloning: A Laboratory Manual,* 2nd Ed., ed. Sambrook et al. (Cold Spring Harbor Laboratory Press, 1989) Chapters 16 and 17). Typically, expression constructs will contain one or more selectable markers, including, but not limited to, the gene that encodes dihydrofolate reductase and the genes that confer resistance to neomycin, tetracycline, ampicillin, chloramphenicol, kanamycin and streptomycin resistance.

Prokaryotic and eukaryotic host cells transfected by the described vectors are also provided by this invention. For instance, cells which can be transfected with the vectors of the present invention include, but are not limited to, bacterial cells such as *E. coli* (e.g., *E. coli* K12 strains, *Streptomyces, Pseudomonas, Serratia marcescens* and *Salmonella typhimurium*, insect cells (baculovirus), including *Drosophila*, fungal cells, such as yeast cells, plant cells and mammalian cells, such as thymocytes, Chinese hamster ovary cells (CHO), and COS cells.

Thus, a nucleic acid molecule described herein can be used to produce a recombinant form of the encoded protein or polypeptide via microbial or eukaryotic cellular processes. Ligating the polynucleic acid molecule into a gene construct, such as an expression vector, and transforming or transfecting into hosts, either eukaryotic (yeast, avian, insect, plant or mammalian) or prokaryotic (bacterial cells), are standard procedures used in producing other well known proteins. Similar procedures, or modifications thereof, can be employed to prepare recombinant proteins according to the present invention by microbial means or tissue-culture technology. Accordingly, the invention pertains to the production of encoded proteins or polypeptides by recombinant technology, as well as to the recombinant host cells themselves.

For example, cells which, in nature, lack CD2BP2 protein expression and activity can be engineered to express the CD2BP2 protein of the invention by gene therapy methods. For example, DNA encoding the CD2BP2 protein, or an active fragment or derivative thereof, can be introduced into an expression vector, such as a viral vector, and the vector can be introduced into appropriate cells which lack CD2BP2 protein expression in an animal. In such a method, a cell population can be engineered to inducibly or constitutively express active CD2BP2 protein. In a preferred embodiment, the vector is delivered to a hematopoietic tissue, such as the bone marrow as described in Corey et al. (*Science* 244: 1275–1281 (1989)).

The proteins and polypeptides of the present invention can be isolated or purified (e.g., to homogeneity) from recombinant cell culture by a variety of processes. These include, but are not limited to, anion or cation exchange chromatography, ethanol precipitation, affinity chromatography and high performance liquid chromatography (HPLC). The particular method used will depend upon the properties of the polypeptide and the selection of the host cell; appropriate methods will be readily apparent to those skilled in the art.

The present invention also relates to antibodies which bind a polypeptide or protein of the invention. For instance, polyclonal and monoclonal antibodies, including non-human and human antibodies, humanized antibodies, chimeric antibodies and antigen-binding fragments thereof (*Current Protocols in Immunology*, John Wiley & Sons, N.Y. (1994); EP Application 173,494 (Morrison); International Patent Application WO86/01533 (Neuberger); and U.S. Pat. No. 5,225,539 (Winters)) which bind to the described protein or polypeptide are within the scope of the invention. A mammal, such as a mouse, rat, hamster or rabbit, can be immunized with an immunogenic form of the protein (e.g., the full length protein or a polypeptide comprising an antigenic fragment of the protein which is capable of eliciting an antibody response). Techniques for conferring immunogenicity on a protein or polypeptide include conjugation to carriers or other techniques well known in the art. The protein or polypeptide can be administered in the presence of an adjuvant. The progress of immunization can be monitored by detection of antibody titers in plasma or serum. Standard ELISA or other immunoassays can be used with the immunogen as antigen to assess the levels of antibody.

Following immunization, anti-peptide antisera can be obtained, and if desired, polyclonal antibodies can be isolated from the serum. Monoclonal antibodies can also be produced by standard techniques which are well known in the art (Kohler and Milstein, *Nature* 256:495–497 (1975); Kozbar et al., *Immunology Today* 4:72 (1983); and Cole et al., *Monoclonal Antibodies and Cancer Therapy*, Alan R. Liss, Inc., pp. 77–96 (1985)). The term "antibody" as used herein is intended to include fragments thereof, such as Fab and F(ab)$_2$. Antibodies described herein can be used to inhibit the activity of the polypeptides and proteins described herein, particularly in vitro and in cell extracts, using methods known in the art. Additionally, such antibodies, in conjunction with a label, such as a radioactive label, can be used to assay for the presence of the expressed protein in a cell from, e.g., a tissue sample, and can be used in an immunoabsorption process, such as an ELISA, to isolate the protein or polypeptide. Tissue samples which can be assayed include human tissues, e.g., differentiated and non-differentiated cells. Examples include, blood, embryonic tissue, dennis, hypodermis and epidermis. These antibodies are useful in diagnostic assays, or as an active ingredient in a pharmaceutical composition.

The invention further provides kits comprising at least all or a portion of the nucleic acid molecules as described herein. Often, the kits contain one or more pairs of oligonucleotides which hybridize to a particular nucleotide sequence. In some kits, the oligonucleotides are provided immobilized to a substrate. For example, the same substrate can comprise oligonucleotide probes for detecting at least 10, 100 or more nucleic acid sequences. Optional additional components of the kit include, for example, restriction enzymes, reverse-transcriptase or polymerase, the substrate nucleoside triphosphates, means used to label (for example, an avidin-enzyme conjugate and enzyme substrate and chromogen if the label is biotin), and the appropriate buffers for reverse transcription, PCR, or hybridization reactions. Usually, the kit also contains instructions for carrying out the methods.

The present invention also relates to an assay for identifying agents which alter (e.g., inhibit or enhance) the activity of the CD2BP2 protein. For example, a cell or cell lysate containing the CD2BP2 protein, or an active portion or derivative thereof, can be contacted with an agent to be tested, and the level of CD2BP2 protein activity, as described herein, can be assessed and compared with the corresponding level in a control in the absence of the agent to be tested. The protein can be contacted directly with the agent to be tested, or a composition, e.g., a cell or cell lysate thereof, comprising the CD2BP2 protein (or active fragment or derivative) can be contacted with the agent to be tested. Inhibition of CD2BP2 protein activity relative to a control indicates that the agent is an antagonist of CD2BP2 protein activity; enhancement of CD2BP2 protein activity relative to a control indicates that the agent is an agonist of CD2BP2 protein activity.

As used herein, "inhibition" of CD2BP2 protein activity is intended to encompass any decrease in CD2BP2 protein expression or activity, whether brought about by decrease in the activity of the CD2BP2 protein itself, by decrease in the amount of CD2BP2 protein present, or by increase in the amount or activity of an inhibitor of CD2BP2 protein. Inhibitors of CD2BP2 protein activity include agents that decrease expression of CD2BP2 mRNA or translation of CD2BP2 protein; agents that interfere with the interaction between CD2 and CD2BP2 (for example, an antibody that binds to the binding domains of CD2 and/or CD2BP2 identified herein); and agents that compete with CD2BP2 protein (for example, a mutant CD2BP2 protein that binds to CD2, yet does not have a cellular effect).

As used herein, "enhancement" of CD2BP2 protein activity is intended to encompass any increase in CD2BP2 protein expression or activity, whether brought about by increase in the activity of the protein itself, or by increase in the amount of protein or mimic present, or both. As used herein, "mimic" is intended to mean an agent which has the same activity as (or mimics) the CD2BP2 protein; "mimics" include active fragments or derivatives, or other variants of the CD2BP2 protein, as described above. Enhancers of CD2BP2 protein activity include agents that enhance expression of CD2BP2 mRNA or translation of CD2BP2 protein (for example, exogenous nucleic acid encoding CD2BP2 protein); and agents that enhance the interaction between CD2 and CD2BP2 (for example, an agent that increases CD2BP2 protein binding to CD2, or which decreases the disassociation of CD2BP2 protein from CD2).

The present invention also relates to agents identified by the assay described above. Agents identified by the assay described herein may inhibit (e.g., shorten or decrease) or enhance (e.g., prolong or increase) the activity of the CD2BP2 protein. The invention further pertains to methods of inhibiting the activity of the CD2BP2 protein, as well as to methods of enhancing the activity of the CD2BP2 protein, such as by contacting the CD2BP2 protein with a CD2BP2 protein antagonist or a CD2BP2 protein agonist as described above.

The invention further pertains to methods of identifying agents which modulate (i.e., inhibit or enhance) signal transduction or cell adhesion. Agents which modulate (inhibit or enhance) CD2BP2 protein activity will consequently modulate signal transduction or cell adhesion. In an assay to identify an agent which modulates signal transduction or cell adhesion, for example, a cell or cell lysate containing the CD2BP2 protein, or an active fragment or derivative thereof, can be contacted with an agent to be tested, and the level of CD2BP2 protein activity, as described above, can be assessed and compared with the corresponding level in a control in the absence of the agent to be tested. The protein can be contacted directly with the agent to be tested, or a composition, e.g., cell or cell lysate thereof comprising the CD2BP2 protein (or active fragment or derivative) can be contacted with the agent to be tested. Modulation of CD2BP2 protein activity relative to a control indicates that the agent modulates CD2BP2 protein activity, and is therefore modulates signal transduction or cell adhesion. The invention further pertains to methods of modulating (enhancing or inhibiting) signal transduction of cell adhesion by modulating (inhibiting or enhancing) the activity of the CD2BP2 protein. For example, the activity of the CD2BP2 protein can be modulated by contacting the CD2BP2 protein with a CD2BP2 protein antagonist or a CD2BP2 protein agonist as described above.

Inhibition of CD2BP2 protein activity, as described above, can be useful in prolonging cell adhesion or enhancing signal transduction; prolonging cell adhesion and/or enhancing signal transduction can be used in cancer therapy, to augment the immune response to cancerous cells and tumors. Enhancement of CD2BP2 protein activity, as described above, can be useful in reducing cell adhesion or inhibiting signal transduction. This is particularly useful in immunocompromised individuals, and in immunodeficiency related diseases.

Furthermore, the invention pertains to methods of identifying agents which modulate (i.e., inhibit or enhance) CD2-triggered IL-2 production. Agents which modulate (inhibit or enhance) CD2BP2 protein activity will consequently modulate CD2-triggered IL-2 production. In an assay to identify an agent which modulates CD2-triggered IL-2 production, for example, a cell or cell lysate containing the CD2BP2 protein, or an active fragment or derivative thereof, can be contacted with an agent to be tested, and the level of CD2BP2 protein activity, as described above, can be assessed and compared with the corresponding level in a control in the absence of the agent to be tested. The protein can be contacted directly with the agent to be tested, or a composition, e.g., cell or cell lysate thereof comprising the CD2BP2 protein (or active fragment or derivative) can be contacted with the agent to be tested. Modulation of CD2BP2 protein activity relative to a control indicates that the agent modulates CD2BP2 protein activity, and is therefore modulates IL-2 production. The invention further pertains to methods of modulating (enhancing or inhibiting) IL-2 production by modulating (inhibiting or enhancing) the activity of the CD2BP2 protein. For example, the activity of the CD2BP2 protein can be modulated by contacting the CD2BP2 protein with a CD2BP2 protein antagonist or a CD2BP2 protein agonist as described above.

The invention provides a method (also referred to herein as a "screening assay") for identifying modulators, i.e., candidate or test compounds or agents (e.g., antisense, polypeptides, peptidomimetics, small molecules or other drugs) which bind to nucleic acid molecules, polypeptides or proteins described herein or which alter (e.g., have a stimulatory or inhibitory effect on), for example, expression or activity of the nucleic acid molecules, polypeptides or proteins of the invention, or physiological responses triggered thereby.

In one embodiment, the invention provides assays for screening candidate or test compounds which bind to or modulate the activity of protein or polypeptide described herein or biologically active portion thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to polypeptide libraries, while the other four approaches are applicable to polypeptide, non-peptide oligomer or small molecule libraries of compounds (Lam, *Anticancer Drug Des.* 12:145 (1997)).

Examples of methods for the synthesis of molecular libraries can be found in the art, for example in DeWitt et al. (1993) *Proc. Natl. Acad. Sci. U.S.A.*, 90:6909; Erb et al. (1994) *Proc. Natl. Acad. Sci. U.S.A.*, 91:11422; Zuckermann et al. (1994). *J. Med. Chem.*, 37:2678; Cho et al.(1993) *Science*, 261:1303; Carell et al. (1994) *Angew. Chem. Int. Ed. Engl.*, 33:2059; Carell et al. (1994) *Angew. Chem. Int. Ed. Engl.*, 33:2061; and in Gallop et al. (1994) *J. Med. Chem.*, 37:1233.

Libraries of compounds may be presented in solution (e.g., Houghten(1992)*Biotechniques*, 13:412–421), or on beads (Lam(1991) *Nature*, 354:82–84), chips (Fodor (1993) *Nature*, 364;555–556), bacteria(Ladner U.S. Pat. No. 5,223,409), spores (Ladner U.S. Pat. No. '409), plasmids (Cull et al.(1992) *Proc. Natl. Acad. Sci. U.S.A.*, 89:1865–1869) or on phage (Scott and Smith (1990) *Science*, 249:386–390); (Devlin (1990) *Science*, 249:404–406); (Cwirla et al. (1990) *Proc. Natl. Acad. Sci.*, 97:6378–6382); (Felici (1991) *J. Mol. Biol.*, 222:301–310); (Ladner supra).

In one embodiment, an assay is a cell-based assay in which a cell which expresses an encoded protein (e.g., CD2, CD2BP2) is contacted with a test compound and the ability of the test compound to bind to the protein is determined. The cell, for example, can be of mammalian origin, such as a T cell. Determining the ability of the test compound to bind to the receptor can be accomplished, for example, by coupling the test compound with a radioisotope or enzymatic label such that binding of the test compound to the receptor can be determined by detecting the labeled with $^{125}$I, $^{35}$S, $^{14}$C, or $^{3}$H, either directly or indirectly, and the radioisotope detected by direct counting of radioemission or by scintillation counting. Alternatively, test compounds can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a test compound to interact with the protein without the labeling of any of the interactants. For example, a microphysiometer can be used to detect the interaction of a test compound with the protein without the labeling of either the test compound or the receptor. McConnell, H. M. et al. (1992) *Science*, 257:1906–1912. As used herein, a "microphysiometer" (e.g., Cytosensor™) is an analytical instrument that measures the rate at which a cell acidifies its environment using a light-addressable potentiometric sensor (LAPS). Changes in this acidification rate can be used as an indicator of the interaction between ligand binding pairs.

In one embodiment, the assay comprises contacting a cell which expresses an encoded protein described herein with a ligand or biologically-active portion thereof, to form an assay mixture, contacting the assay mixture with a test compound, and determining the ability of the test compound to interact with the protein or ligand, wherein determining the ability of the test compound to interact with the protein or ligand comprises determining the ability of the test compound to preferentially bind to the protein or ligand as compared to the ability of the ligand, or a biologically active portion thereof, to bind to the receptor.

In another embodiment, an assay is a cell-based assay comprising contacting a cell expressing a particular target molecule described herein with a test compound and determining the ability of the test compound to modulate or alter (e.g., stimulate/enhance or inhibit) the activity of the target molecule. Determining the ability of the test compound to modulate the activity of the target molecule can be accomplished, for example, by determining the ability of a known ligand to bind to or interact with the target molecule.

Determining the ability of the known ligand to bind to or interact with the target molecule can be accomplished by one of the methods described above for determining direct binding. In a preferred embodiment, determining the ability of the known ligand to bind to or interact with the target molecule can be accomplished by determining the activity of the target molecule. For example, the activity of the target molecule can be determined by detecting induction of a cellular second messenger of the target (e.g., intracellular $Ca^{2+}$, diacylglycerol, $IP_3$, etc.), detecting catalytic/enzymatic activity of the target an appropriate substrate, detecting the induction of a reporter gene (comprising a target-responsive regulatory element operatively linked to a nucleic acid encoding a detectable marker, e.g., luciferase, β-gal), or detecting a cellular response, for example, development, differentiation, rate of proliferation or IL-2 production.

In yet another embodiment, an assay of the present invention is a cell-free assay in which protein of the invention or biologically active portion thereof is contacted with a test compound and the ability of the test compound to bind to the protein or biologically active portion thereof is determined. Binding of the test compound to the protein can be determined either directly or indirectly as described above. In one embodiment, the assay includes contacting the protein or biologically active portion thereof with a known compound which binds the protein to form an assay mixture, contacting the assay mixture with a test compound, and determining the ability of the test compound to interact with the protein. Determining the ability of the test compound to interact with the protein comprises determining the ability of the test compound to preferentially bind to the protein or biologically active portion thereof as compared to the known compound.

In another embodiment, the assay is a cell-free assay in which a protein of the invention or biologically active portion thereof is contacted with a test compound and the ability of the test compound to modulate or alter (e.g., stimulate/enhance or inhibit) the activity of the protein or biologically active portion thereof is determined. Determining the ability of the test compound to modulate the activity of the protein can be accomplished, for example, by determining the ability of the protein to bind to a known target molecule by one of the methods described above for determining direct binding. Determining the ability of the protein to bind to a target molecule can also be accomplished using a technology such as real-time Bimolecular Interaction Analysis (BIA). Sjolander, S. and Urbaniczky, C. (1991) *Anal. Chem.*, 63:2338–2345 and Szabo et al. (1995) *Curr. Opin. Struct. Biol.*, 5:699–705. As used herein, "BIA" is a technology for studying biospecific interactions in real time, without labeling any of the interactants (e.g., BIAcore™). Changes in the optical phenomenon surface plasmon resonance (SPR) can be used as an indication of real-time reactions between biological molecules.

In an alternative embodiment, determining the ability of the test compound to modulate the activity of a protein of the invention can be accomplished by determining the ability of the protein to further modulate the activity of a target molecule. For example, the catalytic/enzymatic activity of the target molecule on an appropriate substrate can be determined as previously described.

In yet another embodiment, the cell-free assay involves contacting a protein of the invention or biologically active portion thereof with a known compound which binds the protein to form an assay mixture, contacting the assay mixture with a test compound, and determining the ability of the test compound to interact with the protein, wherein determining the ability of the test compound to interact with the protein comprises determining the ability of the protein to preferentially bind to or modulate the activity of a target molecule.

The cell-free assays of the present invention are amenable to use of both soluble and/or membrane-bound forms of isolated proteins. In the case of cell-free assays in which a membrane-bound form an isolated protein is used it may be desirable to utilize a solubilizing agent such that the membrane-bound form of the isolated protein is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® 100, Triton® X-114, Thesit®, Isotridecypoly(ethylene glycol ether)$_n$, 3-[(3-cholamidopropyl)dimethylamminio]-1-propane sulfonate (CHAPS), 3-[(3-cholamidopropyl)dimethylamminio]-2-hydroxy-1-propane sulfonate (CHAP SO), or N-dodecyl-N,N-dimethyl-3-ammonio-1-propane sulfonate.

In more than one embodiment of the above assay methods of the present invention, it may be desirable to immobilize either the protein or its target molecule to facilitate separation of complexed from uncomplexed forms of one or both of the proteins, as well as to accommodate automation of the assay. Binding of a test compound to the protein, or interaction of the protein with a target molecule in the presence and absence of a candidate compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the proteins to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the test compound or the test compound and either the non-adsorbed target protein or protein of the invention, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of binding or activity determined using standard techniques.

Other techniques for immobilizing proteins on matrices can also be used in the screening assays of the invention. For example, either a protein of the invention or a target molecule can be immobilized utilizing conjugation of biotin and streptavidin. Biotinylated protein of the invention or target molecules can be prepared from biotin-NHS(N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with a protein of the invention or target molecules, but which do not interfere with binding of the protein to its target molecule, can be derivatized to the wells of the plate, and unbound target or protein trapped in the wells by antibody conjugation. Methods for detecting such complexes, in addition to those described above for the GST-immobilized complexes, include immunodetection of complexes using antibodies reactive with the protein or target molecule, as well as enzyme-linked assays which rely on detecting an enzymatic activity associated with the protein or target molecule.

In another embodiment, modulators of expression of nucleic acid molecules of the invention are identified in a method wherein a cell is contacted with a candidate compound and the expression of appropriate mRNA or protein in the cell is determined. The level of expression of appropriate mRNA or protein in the presence of the candidate compound is compared to the level of expression of mRNA or protein in the absence of the candidate compound. The candidate compound can then be identified as a modulator of expression based on this comparison. For example, when expression of mRNA or protein is greater (statistically significantly greater) in the presence of the candidate compound than in its absence, the candidate compound is identified as a stimulator or enhancer of the mRNA or protein expression. Alternatively, when expression of the mRNA or protein is less (statistically significantly less) in the presence of the candidate compound than in its absence, the candidate compound is identified as an inhibitor of the mRNA or protein expression. The level of mRNA or protein expression in the cells can be determined by methods described herein for detecting mRNA or protein.

In yet another aspect of the invention, the proteins of the invention can be used as "bait proteins" in a two-hybrid assay or three-hybrid assay (see, e.g., U.S. Pat. No. 5,283, 317; Zervos et al. (1993) *Cell*, 72:223–232; Madura et al. (1993) *J. Biol. Chem.*, 268:12046–12054; Bartel et al. (1993) *Biotechniques*, 14:920–924; Iwabuchi et al. (1993) *Oncogene*, 8:1693–1696; and Brent WO94/10300), to identify other proteins (captured proteins) which bind to or interact with the proteins of the invention and modulate their activity. Such captured proteins are also likely to be involved in the propagation of signals by the proteins of the invention as, for example, downstream elements of a protein-mediated signaling pathway. Alternatively, such captured proteins are likely to be cell-surface molecules associated with non-protein-expressing cells, wherein such captured proteins are involved in signal transduction.

The two-hybrid system is based on the modular nature of most transcription factors, which consist of separable DNA-binding and activation domains. Briefly, the assay utilizes two different DNA constructs. In one construct, the gene that codes for a protein of the invention is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming an protein-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected, and cell colonies containing the functional transcription factor can be isolated and used to obtain the cloned gene which encodes the protein which interacts with the protein of the invention.

This invention further pertains to novel agents identified by the above-described screening assays. Accordingly, it is within the scope of this invention to further use an agent identified as described herein in an appropriate animal model. For example, an agent identified as described herein (e.g., a modulating agent, an antisense nucleic acid molecule, a specific antibody, or a protein-binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining protein and/or nucleic acid expression as well as activity of proteins of the invention, in the context of a biological sample (e.g., blood, serum, cells, tissue) to thereby determine whether an individual is afflicted with a disease or disorder, or is at risk of developing a disorder, associated with aberrant expression or activity, e.g., of CD2BP2 or of CD2. The invention also provides for prognostic (or predictive) assays for determining whether an individual is at risk of developing a disorder associated with activity or expression of proteins or nucleic acids of the invention.

Disorders which may be treated or diagnosed by methods described herein include, but are not limited to, autoimmune diseases, such as rheumatoid arthritis, multiple sclerosis, juvenile diabetes, and systemic lupus erythomatosis, as well as in transplantation to reduce adhesion of the recipient's T cells with tissues in the autograft. Other disorders include those in which it is desirable to inhibit CD2-triggered inflammation.

For example, mutations in a specified gene can be assayed in a biological sample. Such assays can be used for prognostic or predictive purpose to thereby phophylactically treat an individual prior to the onset of a disorder characterized by or associated with expression or activity of nucleic acid molecules or proteins of the invention.

Another aspect of the invention pertains to monitoring the influence of agents (e.g., drugs, compounds) on the expression or activity of proteins of the invention in clinical trials.

An exemplary method for detecting the presence or absence of proteins or nucleic acids of the invention in a biological sample involves obtaining a biological sample from a test subject and contacting the biological sample with a compound or an agent capable of detecting the protein, or nucleic acid (e.g., mRNA, genomic DNA) that encodes the protein, such that the presence of the protein or nucleic acid is detected in the biological sample. A preferred agent for detecting mRNA or genomic DNA is a labeled nucleic acid probe capable of hybridizing to mRNA or genomic DNA sequences described herein. The nucleic acid probe can be, for example, a full-length nucleic acid, or a portion thereof, such as an oligonucleotide of at least 6, 15, 17, 30, 50, 100, 250 or 500 nucleotides in length and sufficient to specifically hybridize under stringent conditions to appropriate mRNA or genomic DNA. For example, the nucleic acid probe can be all or a portion of SEQ ID NO: 1, or the complement of SEQ ID NO: 1, or a portion thereof. Other suitable probes for use in the diagnostic assays of the invention are described herein.

A preferred agent for detecting proteins of the invention is an antibody capable of binding to the protein, preferably an antibody with a detectable label. Antibodies can be polyclonal, or more preferably, monoclonal. An intact antibody, or a fragment thereof (e.g., Fab or $F(ab')_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, calls and biological fluids isolated from a subject, as well as tissues, cells and fluids present within a subject. That is, the detection method of the invention can be used to detect mRNA, protein, or genomic DNA of the invention in a biological sample in vitro as well as in vivo. For example, in vitro techniques for detection of mRNA include Northern hybridizations and in situ hybridizations. In vitro techniques for detection of protein include enzyme linked immunosorbent assays (ELISAs), Western blots, immunoprecipitations and immunofluorescence. In vitro techniques for detection of genomic DNA include Southern hybridizations. Furthermore, in vivo techniques for detection of protein include introducing into a subject a labeled anti-protein antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a serum sample or tissue biopsy isolated by conventional means from a subject.

In another embodiment, the methods further involve obtaining a control biological sample from a control subject, contacting the control sample with a compound or agent capable of detecting protein, mRNA, or genomic DNA of the invention, such that the presence of protein, mRNA or genomic DNA is detected in the biological sample, and comparing the presence of protein, mRNA or genomic DNA in the control sample with the presence of protein, mRNA or genomic DNA in the test sample.

The invention also encompasses kits for detecting the presence of proteins or nucleic acid molecules of the invention in a biological sample. For example, the kit can comprise a labeled compound or agent capable of detecting protein or mRNA in a biological sample; means for determining the amount of in the sample; and means for comparing the amount of in the sample with a standard. The compound or agent can be packaged in a suitable container. The kit can further comprise instructions for using the kit to detect protein or nucleic acid.

The present invention also pertains to pharmaceutical compositions comprising polypeptides and other compounds described herein. For instance, a polypeptide or protein, or prodrug thereof, of the present invention can be formulated with a physiologically acceptable medium to prepare a pharmaceutical composition. The particular physiological medium may include, but is not limited to, water, buffered saline, polyols (e.g., glycerol, propylene glycol, liquid polyethylene glycol) and dextrose solutions. The optimum concentration of the active ingredient(s) in the chosen medium can be determined empirically, according to well known procedures, and will depend on the ultimate pharmaceutical formulation desired. Methods of introduction of exogenous polypeptides at the site of treatment include, but are not limited to, intradermal, intramuscular, intraperitoneal, intravenous, subcutaneous, oral and intranasal. Other suitable methods of introduction can also include gene therapy, rechargeable or biodegradable devices, viral vectors, naked DNA and slow release polymeric devices. The pharmaceutical compositions of this invention can also be administered as part of a combinatorial therapy with other agents. Nucleic acid sequences of the invention can be used in gene therapy and introduced either in vivo or ex vivo into cells for expression in a mammalian subject.

The diagnostic methods described herein can furthermore be utilized to identify subjects having or at risk of developing a disease or disorder associated with aberrant expression or activity of proteins and nucleic acid molecules of the invention. For example, the assays described herein, such as the preceding diagnostic assays or the following assays can be utilized to identify a subject having or at risk of developing a disorder associated with protein or nucleic acid expression or activity such as a proliferative disorder, a differentiative or developmental disorder, or a poietic disorder. Alternatively, the prognostic assays can be utilized to identify a subject having or at risk for developing a differentiative or proliferative disease (e.g., cancer) particularly of the prostate. Thus, the present invention provides a method for identifying a disease or disorder associated with aberrant expression or activity of proteins or nucleic acid molecules of the invention, in which a test sample is obtained from a subject and protein or nucleic acid (e.g., mRNA, genomic DNA) is detected, wherein the presence of protein or nucleic acid is diagnostic for a subject having or at risk of developing a disease or disorder associated with aberrant expression or activity of the protein or nucleic acid sequence of the invention. As used herein, a "test sample" refers to a biological sample obtained from a subject of interest. For example, a test sample can be a biological fluid (e.g., serum), cell sample, or tissue (e.g., spleen tissue).

Furthermore, the prognostic assays described herein can be used to determine whether a subject can be administered an agent (e.g., an agonist, antagonist, peptidomimetic, protein, polypeptide, nucleic acid, small molecule, or other drug candidate) to treat a disease or disorder associated with aberrant expression or activity of a protein or nucleic acid molecule of the invention. For example, such methods can be used to determine whether a subject can be effectively treated with an agent for a disorder, such as a proliferative disorder, a differentiative or a developmental disorder. Alternatively, such methods can be used to determine whether a subject can be effectively treated with an agent for a differentiative or proliferative disease (e.g., cancer). Thus, the present invention provides methods for determining whether a subject can be effectively treated with an agent for a disorder associated with aberrant expression or activity of a protein or nucleic acid of the present invention, in which a test sample is obtained and protein or nucleic acid expression or activity is detected (e.g., wherein the abundance of particular protein or nucleic acid expression or activity is diagnostic for a subject that can be administered the agent to treat a disorder associated with aberrant expression or activity.)

The methods of the invention can also be used to detect genetic alterations in genes or nucleic acid molecules of the present invention, thereby determining if a subject with the altered gene is at risk for a disorder characterized by aberrant development, aberrant cellular differentiation, aberrant cellular proliferation or an aberrant hematopoietic response. In preferred embodiments, the methods include detecting, in a sample of cells from the subject, the presence or absence of a genetic alteration characterized by at least one of an alteration affecting the integrity of a gene encoding a particular protein, or the mis-expression of the gene. For example, such genetic alterations can be detected by ascertaining the existence of at least one of (1) a deletion of one or more nucleotides; (2) an addition of one or more nucleotides; (3) a substitution of one or more nucleotides, (4) a chromosomal rearrangement; (5) an alteration in the level of a messenger RNA transcript; (6) aberrant modification, such as of the methylation pattern of the genomic DNA; (7) the presence of a non-wild type splicing pattern of a messenger RNA transcript; (8) a non-wild type level; (9) allelic loss; and (10) inappropriate post-translational modification. As described herein, there are a large number of assay techniques known in the art which can be used for detecting alterations in a particular gene. A preferred biological sample is a tissue or serum sample isolated by conventional means from a subject.

In certain embodiments, detection of the alteration involves the use of a probe/primer in a polymerase chain reaction (PCR) (see, e.g., U.S. Pat. Nos. 4,683,195 and 4,683,202), such an anchor PCR or RACE PCR, or, alternatively, in a ligation chain reaction (LCR) (see, e.g., Landegran et al. (1988) *Science,* 241:1077–1080; and Nakazawa et al. (1994) *PNAS,* 91:360–364), the latter of which can be particularly useful for detecting point mutations (see Abravaya et al. (1995) *Nucleic Acids Res.,* 23:675–682). This method can include the steps of collecting a sample of cells from a patient, isolating nucleic acid (e.g., genomic, mRNA or both) from the cells of the sample, contacting the nucleic acid sample with one or more primers which specifically hybridize to the gene under conditions such that hybridization and amplification of the gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al. (1990) *Proc. Natl. Acad. Sci. USA,* 87:1874–1878), transcriptional amplification system (Kwoh, D. Y. et al., (1989) *Proc. Natl. Acad. Sci. USA,* 86:1173–1177), Q-Beta Replicase (Lizardi, P. M. et al.,(1988) *Bio/Technology,* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a given gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for sample, U.S. Pat. No. 5,498,531) ca be used to score for the presence of specific mutations by development or loss of a ribozyme cleavage site.

In other embodiments, genetic mutations can be identified by hybridizing a sample and control nucleic acids, e.g., DNA or RNA, to high density arrays containing hundreds or thousands of oligonucleotide probes (Cronin, M. T. et al. (1996) *Human Mutation*, 7:244–255; Kozal, M. J. et al. (1996) *Nature Medicine*, 2:753–759). For example, genetic mutations can be identified in two dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the gene and detect mutations by comparing the sequence of the gene from the sample with the corresponding wild-type (control) gene sequence. Examples of sequencing reactions include those based on techniques developed by Maxim and Gilbert ((1997) *PNAS*, 74:560) or Sanger ((1977) *PNAS*, 74:5463). It is also contemplated that any of a variety of automated sequencing procedures can be utilized when performing the diagnostic assays ((1995) *Biotechniques*, 19:448), including sequencing by mass spectrometry (see, e.g., PCT International Publication No. WO 94/16101; Cohen et al. (1996) *Adv. Chromatogr.*, 36:127–162; and Griffin et al. (1993) *Appl. Biochem. Biotechnol.*, 38:147–159).

Other methods for detecting mutations include methods in which protection from cleavage agents is used to detect mismatched bases in RNA/RNA or RNA/DNA heteroduplexes (Myers et al. (1985) *Science*, 230:1242). In general, the art technique of "mismatch cleavage" starts by providing heteroduplexes of formed by hybridizing (labeled) RNA or DNA containing the wild-type sequence with potentially mutant RNA or DNA obtained from a tissue sample. The double-standard duplexes are treated with an agent which cleaves single-stranded regions of the duplex such as which will exist due to base pair mismatches between the control and sample strands. For instance, RNA/DNA duplexes can be treated with Rnase and DNA/DNA hybrids treated with SI nuclease to enzymatically digest the mismatched regions. After digestion of the mismatched regions, the resulting material is then separated by size on denaturing polyacrylamide gels to determine the site of mutation. See, for example Cotton et al. (1988) *Proc. Natl. Acad. Sci. USA*, 85:4397; Saleeba et al. (1992) *Methods Enzymol.*, 217: 286–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis*, 15:1657–1662). According to an exemplary embodiment, a probe based on an nucleotide sequence of the invention is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in genes. For example, single strand conformation polymorphism (SSCP) may be used to detect differences in electrophoretic mobility between mutant and wild type nucleic acids (Orita et al. (1989) *Proc. Natl. Acad. Sci. USA*, 86:2766, see also Cotton (1993) *Mutat Res*, 285:125–144; and Hayashi (1992) *Genet Anal. Tech. Appl.*, 9:73–79). Single-stranded DNA fragments of sample and control nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet.*, 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature*, 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys. Chem.*,265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature*, 324:163); Saiki et al. (1989) *Proc. Natl. Acad. Sci. USA*, 86:6320). Such allele-specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.,* 17:2437–2448) or at the extreme 3' end of one primer where, under appropriate conditions, mismatch can prevent, or reduce polymerase extension (Prossner (1993) *Tibtech,* 11:238). In addition it may be desirable to introduce a novel restriction site in the region of the mutation to create cleavage-based detection (Gasparini et al. (1992) *Mol. Cell Probes,* 6:1). It is anticipated that in certain embodiments amplification may also be performed using Taq ligase for amplification (Barany (1991) *Proc. Natl. Acad. Sci. USA,* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a gene of the present invention. Any cell type or tissue in which the gene is expressed may be utilized in the prognostic assays described herein.

In one aspect, the invention provides a method for preventing in a subject, a disease or condition associated with aberrant expression or activity of genes or proteins of the present invention, by administering to the subject an agent which modulates expression or at least one activity of a gene or protein of the invention. Subjects at risk for a disease which is caused or contributed to by aberrant gene expression or protein activity can be identified by, for example, any or a combination of diagnostic or prognostic assays as described herein. Administration of a prophylactic agent can occur prior to the manifestation of symptoms characteristic of the aberrancy, such that a disease or disorder is prevented or, alternatively, delayed in its progression. Depending on the type of aberrancy, for example, an agonist or antagonist agent can be used for treating the subject. The appropriate agent can be determined based on screening assays described herein.

Cells can also be cultured ex vivo in the presence of proteins of the present invention in order to produce a desired effect on such cells. Treated cells can then be introduced in vivo for therapeutic purposes.

Another aspect of the invention pertains to methods of modulating expression or activity of genes or proteins of the invention for therapeutic purposes. The modulatory method of the invention involves contacting a cell with an agent that modulates one or more of the activities of the specified protein associated with the cell. An agent that modulates protein activity can be an agent as described herein, such as a nucleic acid or a protein, a naturally-occurring target molecule of a protein described herein, a polypeptide, a peptidomimetic, or other small molecule. In one embodiment, the agent stimulates one or more protein activities. Examples of such stimulatory agents include active protein as well as a nucleic acid molecule encoding the protein that has been introduced into the cell. In another embodiment, the agent inhibits one or more protein activities. Examples of such inhibitory agents include antisense nucleic acid molecules and anti-protein antibodies. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant expression or activity of a protein or nucleic acid molecule of the invention. In one embodiment, the method involves administering an agent (e.g., an agent identified by a screening assay described herein), or combination of agents that modulates (e.g., upregulates or downregulates) expression or activity of a gene or protein of the invention. In another embodiment, the method involves administering a protein or nucleic acid molecule of the invention as therapy to compensate for reduced or aberrant expression or activity of the protein or nucleic acid molecule.

Stimulation of protein activity is desirable in situations in which the protein is abnormally downregulated and/or in which increased protein activity is likely to have a beneficial effect. Likewise, inhibition of protein activity is desirable in situations in which the protein is abnormally upregulated and/or in which decreased protein activity is likely to have a beneficial effect. One example of such a situation is where a subject has a disorder characterized by aberrant development or cellular differentiation. The molecules of the present invention, as well as agents, or modulators which have a stimulatory or inhibitory effect on the protein activity (e.g., gene expression) as identified by a screening assay described herein can be administered to individuals to treat (prophylactically or therapeutically) disorders (e.g., proliferative or developmental disorders) associated with aberrant protein activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a molecule of the invention or modulator thereof, as well as tailoring the dosage and/or therapeutic regimen of treatment with such a molecule or modulator.

Pharmacogenomics deals with clinically significant hereditary variations in the response to drugs due to altered drug disposition and abnormal action in affected persons. See e.g., Eichelbaum, M., *Clin Exp Pharmacol. Physiol.,* (1996) 23(10–11):983–985 and Linder, M. W., Clin. Chem. (1997) 43(2):254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms.

The invention additionally pertains to methods of targeting proteins to a CD2 molecule. Because CD2BP2 protein binds to CD2, CD2BP2 protein can be used to target another protein (a "target protein") or agent to the vicinity of CD2. The target protein or agent is linked to CD2BP2 protein, either chemically or physically, in a manner such that the interaction between CD2BP2 protein and CD2 is not affected (i.e., such that the binding domain of the CD2BP2 protein can still bind with CD2). When the CD2BP2 protein interacts with CD2, the target protein that is linked to the CD2BP2 protein is thereby brought in proximity with CD2 as well.

The invention also relates to a novel method of promoting or enhancing protein-protein interactions. As a result of work described herein, it has been discovered that a motif on CD2 (SEQ ID NO: 10) interacts with (e.g., binds) a motif on CD2BP2 (SEQ ID NO: 9, e.g., SEQ ID NO: 3). This discovery provides a method of enhancing or promoting protein-protein interactions between proteins which bear these motifs. That is, a protein which comprises the motif of SEQ ID NO: 10 will interact with a protein which comprises the motif of SEQ ID NO: 9 (e.g., SEQ ID NO: 3) by virtue of the interaction between the two motifs. The proteins can normally (in nature) comprise the specified motifs or can be proteins which do not normally (in nature) comprise the motifs but which have been engineered to contain them. This method is useful in targeting particular proteins to one another, for example, for co-localization at a particular cellular location, as well as in promoting binding or interaction between the proteins themselves, such as, for example, to transduce a particular cellular signal.

The contents of all references, patents and published patent applications cited throughout this application are hereby incorporated by reference. The invention will be further illustrated by the following Examples, which are not intended to limit the scope of the invention.

EXAMPLE 1

Yeast Two-Hybrid System

The yeast hybrid system interaction trap was used as described (Finley and Brent, *Interaction Trap Cloning with Yeast* (Oxford Univ. Press), NY (1995)). In brief, as bait, a human CD2 cDNA encoding the cytoplasmic segment amino acids 221–327 was transferred into the pEG202 vector. cDNAs from an activated human T cell cDNA library, CD2 binding protein 2 (CD2BP2), or mutant cDNA variants of CD2BP2 were introduced into the pJG4–5 vector between EcoRI and Xho1 restriction sites. Mutations were created by a previously described method (Higuchi et al., *Nucleic Acids Res.* 16:7351–7367 (1988)), and were confirmed by DNA sequencing. Both of the yeast shuttle vectors were introduced into the yeast strain EGY48, were plated onto selection plates containing glucose, and were incubated at 30° C. After 48 hours greater than 100 colonies were mixed, were transferred onto a plate containing galactose/raffinose and 5-bromo-4-chloro-3-indolyl-D-galactoside, and were incubated for 48 hours at 30° C. followed by 5 days at 8° C. The strength of the interaction was scored based on the time point when the blue color appeared in comparison with a negative control: ++++, <6 hours; +++, 12 hours: ++, <24 hours; +, <48 hours; ±, <72 hours; and −, >72 hours. CD2 mutations were generated and analyzed in a similar manner.

5' Rapid Amplification of cDNA Ends (RACE) and PCR

Standard 5' RACE was performed by using human T cell total RNA as described (Frohman, *Methods Enzymol.* 218: 340–356 (1993)). The primers corresponded to position bp 676–697 (for the reverse transcription primer) and bp 356–376 and 310–331 (for RACE primers), according to the numbering in FIG. 1A. The RACE reaction produced a single product as detected by agarose gel electrophoresis. To introduce the Kozak consensus sequence (CCGCCACC; SEQ ID NO: 12) before the initiation ATG as well as FLAG epitope sequence (GACTACAAGGACGACGATGACAAG (SEQ ID NO: 13) encoding DYKDDDDK (SEQ ID NO: 14)) at the N terminus of the CD2BP2 sequence, two consecutive PCR reactions were performed in which the tagged primers extended the 5' end of the product stepwise. As a downstream primer, an oligonucleotide corresponding to bp 676–697 was used. The PCR product then was cloned into the TA cloning vector pCR2.1 (Invitrogen), and the DNA sequence was verified. Subsequently, the 5' DNA fragment (between the EcoRI site within the vector and an endogenous PstI site within the CD2BP2 sequence) was obtained, as was a 3' PstI-Xho1 fragment isolated from the original pJG4–5 CD2BP2 clone. Both of the gel purified fragments were cloned into pCR2.1 (Invitrogen), which previously had been digested with EcoRI-Xhol, thus generating a full length FLAG-CD2BP2 construct.

Transfection, Immunoprecipitation, and Western Blotting

As the vectors for transfection, pcDNA1.1 and pcDNA3.1 (Invitrogen) were used with COS7 and with Jurkat cells, respectively. For expression of CD2 and CD4 in COS7 cells, a pCDM8 plasmid containing each was used (Sakiharna et al, *Proc. Natl. Acad. Sci. USA* 92:6444–6448 (1995); Li et al., *J. Mol. Biol.* 263:209–226 (1996)). COS7 cells were transfected by the calcium phosphate precipitation method as described (Sakihama et al., *Proc. Natl. Acad. Sci. USA* 92:6444–6448 (1995). For immunoblot analysis, $2\times10^6$ COS7 cells or $10^7$ Jurkat transformants were washed with cold TBS (20 mM Tris, pH 7.4/0.15 NaCl), were lysed in TBS containing 1% Triton X-100, 10 mM NaF, 10 mM sodium pyrophosphate, 0.2 trypsin inhibitory units (TIU)/ml aprotinin, 1 mM phenylmethylsulfonl fluoride, 1 mM sodium orthovanadate, 5 µg/ml leupeptin, 1 mM $MgCl_2$, and 1 mM $ZnCl_2$ and were incubated for 2 hours with 15 µl of CNBr Sepharose beads coupled with either 3T4–8B5 (anti-T11) anti-CD2 mAb, 19Thy5D7 anti-CD4, 2H11 anti-leucine zipper mAb, or M2 anti-FLAG mAb agarose beads (Kodak). The bead-bound immune complexes were washed with lysis buffer and TBS and were eluted by boiling in Laemmli SDS sample buffer. Western blotting was performed as described (Johnstone and Thorpe, in *Immunochemistry in Practice* (Blackwell Scientific, Oxford), pp. 211–225 (1996)). For detection of the FLAG epitope, M2 mAb was used. For CD2 detection, M32 rabbit serum was used at 1:2,000, followed by detection with protein A-HRP (Bio-Rad) and ECL (Amersham) according to the manufacturer's protocol.

Protein Expression and NMR Analysis

The CD2BP2 protein used for the NMR studies comprises amino acid residues 256–341 with an additional glycine as well as six histidines placed at the N terminus. The cDNA encoding this sequence was cloned into the T7-based expression vector pTFT74 (Freund et al., *FEBS Lett.,* 320: 97–100 (1993)), and was expressed in the *Escherichia coli* strain BL21 (DE3) (Studier et al., *Methods Enzymol.* 185: 60–89 (1990)). Purification of the soluble cytoplasmic protein was achieved with a single-step purification on Ni-Sepharose (Qiagen). Protein samples were concentrated and buffer exchanged against 50 mM sodium-phosphate buffer (pH 6.3) with Centricon-3-concentrators (Amicon). The glutathione S-transferase (GST)-CD2 construct comprised residues 221–282 of the CD2 molecule fused to the GST gene of the pGEX-4T-1 vector (Pharmacia). The fusion protein was expressed in *E. coli* BL21 (DE3) and was purified by glutathione-Sepharose (Pharmacia) in a single step. Except for prolines, NMR backbone assignments of the isolated CD2BP2 binding domain were achieved by the use of an HNCA experiment (Kay et al., *J. Magn. Reson.*

89:496–514 (1990)) applied to a $^{15}$N—$^{13}$C-labeled sample of the CD2BP2 domain. Starting points for the sequential assignment were obtained by the acquisition of a gradient enhanced version of the HSQC experiment (Mori et al., *J. Magn. Reson. B* 108:94–98 (1995)) by using the WATERGATE sequence for water suppression (Sklenar et al., *J. Magn. Reson.* 102:241–245 (1993)) for selectively labeled samples ($^{15}$N-leucine, $^{15}$N-valine and 15N-phenylalanine). NMR experiments were performed either on a Unity 500 machine (Varian) or a Bruker AM500 spectrometer (Bruker, Billerica, Mass.). Sample concentrations were 1.5 mM for the double-labeled sample and 0.4 mM for the selectively labeled samples. Spectra were measured at 298 K. The data were processed and analyzed with the programs PROSA (Güntert et al., *J. Biomol. NMR* 2:619–630 (1992)) and XEASY (Eccles et al., *J. Biomol. NMR* 1:111–130 (1991)), respectively.

Regulated CD2BP2 Expression and Cell Sorting

Jurkat cells expressing the tetracycline responsive transcription activator (Jurkat-tTA) were generated according to the manufacturer's protocol (Clontech). For expression and sorting analysis, typically, $10^6$ cells were electroporated with 20 μg pBI-G CD2BP2 cDNA by using a cell porator (Bio-Rad) set at 800 μF and 250 V, incubated in standard B' medium [RPMI medium 1640 with 10% fetal calf serum, 2 mM L-glutamine, 1 mM sodium pyruvate, and 50 units/ml penicillin-streptomycin (Gibco/BRL)] for 24 hours and were strained by fluoresence-2-galactopyranoside as described (Nolan and Herzenberg, *Proc. Natl. Acad. Sci. USA* 85:2603–2607 (1988)). In brief, $10^7$ cells were loaded with fluorescence-2-galactopyranoside for 2 minutes at 37° C. in hypoosmotic medium (0.5× RPMI medium 1640/2% fetal calf serum/10 mM Hepes, pH 7.6/0.5 mM fluorescence-2-galactopyranoside) and were returned to normal osmolarity (B' medium) for incubation for 1 hour at 4° C. Cell sorting was performed by using either a Vantage (Becton Dickinson) or MoFlo (Cytomation, Fort Collins, Colo.) cell sorter.

$Ca^{2+}$ Flux and IL-2 Assays $Ca^{2+}$ influx was analyzed as reported (Reem et al., *J. Immunol.* 139:130–134 (1987); Targan et al., *J. Immunol.* 154:664–675 (1995)). For IL-2 production assays, sorted cells were plated onto U-bottom 96-well plates at $10^5$ cells per well in 200 μl of B' medium, which was supplied with 0.5 nM phorbol myristate acetate and, when necessary, either a combination of anti-T11$_2$ plus anti-T11$_3$ anti-CD2 mAbs or anti-CD3 mAb 2Ad2 (1:100 dilution of ascites). After 24 hours, the amount of IL-2 in the medium was assayed by ELISA (Endogen).

EXAMPLE 2

Sample Preparation

The protein fragment of CD2BP2 used in this study comprised the amino acids 256–342 of the entire protein and contained an additional N-terminal hexa-histidine-tag. Protein expression in *E. coli* BL21 (DE3) was achieved by using the T7-promotor based vector pTFT74. Purification of the protein from the soluble fraction was achieved as described above. The GST-fusion protein of the truncated CD2-tail used in binding experiments comprised residues 221–282 of CD2 was expressed and purified as above. The NMR buffer used was 50 mM sodium-phosphate, pH 6.3.

NMR Spectroscopy

All experiments were acquired at 298 K at either Unity 500 or 750 MHz machines or a 500 MHz Bruker AMX 500 instrument. NMR data processing and analysis were carried out as described above. Backbone assignments were obtained with a HNCA experiment. Residue-type based assignments were achieved by the combined use of a $^{15}$N-edited TOCSY recorded with a mixing time of 100 ms and the information from $^{15}$N-leucine, $^{15}$N-valine and $^{15}$N- phenylalanine-labeled samples, respectively. Complete side-chain assignments could be obtained by the analysis of a HCCH-TOCSY experiment, making use of the carbon-α and carbon-β frequencies extracted from a CBCA(CO)NH experiment. NOE constraints were obtained from a 2D NOESY in D$_2$O and a 3D $^{15}$N-NOESY-HSQC experiment in H$_2$O, each with a 60 ms mixing time, and a $^{13}$C-edited NOESY spectrum with a 100 ms mixing. Hydrogen-bond constraints were based on slow NH exchange and NOE's characteristic for regular secondary structure. Dihedral angle constrains were derived from the intensity ratios of diagonal and cross peaks in the HNHA (Vuister and Bax, *J. Am. Chem. Soc.* 115:7772–7777 (1993)) experiment. Stereospecific assignments was obtained for eight methylene groups and stereo specific assignment of the methyl groups of all valines and leucines was achieved by using a 10% $^{13}$C-labeled sample (Senn, et al., *FEBS Lett.* 249:113–118 (1989)).

Structure Calculation

Structure calculations were limited to the folded part (residues 280–341 of CD2BP2), since the first 24 amino acids as well as the N-terminal histidine-tag were identified by their relaxation properties and chemical shift values to be unstructured and no NOE's were found between this unstructured part and the globular domain. Initial structure calculations were performed using the program Dyana (Güntert, et al., *J. Mol. Biol.* 273:283–298 (1997)). Final calculations and structure refinement were obtained by using the program XPLOR (Brünger, *X-PLOR Version 3.1: A system for X-ray Crystallography and NMR* (Yale, Univ. Press, New Haven, (1992)). For the structure calculation 752 interproton distances were used comprising 134 intraresidue, 297 medium-range and 321 long-range distance constraints. In addition, 34 constraints for 17 hydrogen bonds and 77 dihedral angle constraints were used for the structure determination. The average root mean square deviation values from idealized geometry for bonds, angles and impropers are 0.0013 Å, 0.33° and 0.14°, respectively. The 16 structures with lowest energies from a XPLOR (Brünger, *X-PLOR Version 3.1: A system for X-ray Crystallography and NMR* (Yale, Univ. Press, New Haven, (1992)) run with 30 iterations displayed no distance violations greater than 0.3 Å and dihedral restraint violations greater than 5°. The quality of the ensemble of NMR structures was examined with the PROCHECK (Laskowski, et al., *J. Biomol. NMR:* 8:477–486 (1996)) program. The coordinates have been submitted to the Protein Data Bank.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. An isolated nucleic acid molecule which encodes a human CD2BP2 protein comprising SEQ ID NO: 2, having biological activity of binding to a CD2 molecule, or the complement of said nucleic acid molecule.

2. An isolated nucleic acid molecule of claim 1, wherein said nucleic acid molecule has the same nucleotide sequence as endogenous human coding regions encoding the protein of SEQ ID NO: 2, or the complement of said nucleic acid molecule.

3. A nucleic acid construct comprising the isolated nucleic acid molecule of claim 1 operably linked to a regulatory sequence.

4. A recombinant host cell comprising the nucleic acid construct of claim 3.

5. An isolated nucleic acid molecule consisting of a nucleotide sequence encoding the amino acid sequence of SEQ ID NO: 10, or the complement of said nucleic acid molecule.

6. A nucleic acid construct comprising the isolated nucleic acid molecule of claim 5 operably linked to a regulatory sequence.

7. A recombinant host cell comprising the nucleic acid construct of claim 6.

8. A method for preparing a human protein of SEQ ID NO: 2, comprising culturing the recombinant host cell of claim 4.

9. An isolated recombinant nucleic acid molecule comprising a first nucleic acid molecule and a second nucleic acid molecule encoding the amino acid sequence of SEQ ID NO: 3, wherein the first and the second nucleic acid molecules are heterologous, or a complement of the recombinant nucleic acid molecule, and wherein said first nucleic acid molecule encodes a polypeptide selected from the group consisting of polypeptides to assist in isolation or purification, polypeptides to extend half-life and carrier polypeptides.

10. An isolated recombinant nucleic acid molecule comprising a first nucleic acid molecule and a second nucleic acid molecule encoding the amino acid sequence of SEQ ID NO: 10, wherein the first and the second nucleic acid molecules are heterologous, or a complement of the recombinant nucleic acid molecule, and wherein said first nucleic acid molecule encodes a polypeptide selected from the group consisting of polypeptides to assist in isolation or purification, polypeptides to extend half-life and carrier polypeptides.

11. An isolated nucleic acid molecule consisting of a nucleotide sequence encoding the amino acids 1 through 7 of SEQ ID NO: 22, or the complement of said nucleic acid molecule.

12. An isolated nucleic acid molecule which encodes a polypeptide consisting of a fragment of human protein of SEQ ID NO: 2 wherein said fragment comprises the polypeptide of SEQ ID NO: 3, or the complement of said nucleic acid molecule.

13. A nucleic acid construct comprising the isolated nucleic acid molecule of claim 12 operably linked to a regulatory sequence.

14. A recombinant host cell comprising the nucleic acid construct of claim 12.

15. A method for preparing a polypeptide consisting of a fragment of a human protein of SEQ ID NO: 2, wherein said fragment comprises the polypeptide of SEQ ID NO: 3, said method comprising a step of culturing a recombinant host cell of claim 14.

16. An isolated nucleic acid molecule comprising the nucleotide sequence of SEQ ID NO: 1, or the complement thereof.

17. An isolated nucleic acid molecule encoding a polypeptide consisting of a fragment of SEQ ID NO: 2 that comprises SEQ ID NO: 3, having biological activity of binding to a CD2 molecule, or a complement of said nucleic acid molecule.

* * * * *

UNITED STATES PATENT AND TRADEMARK OFFICE
CERTIFICATE OF CORRECTION

| | | |
|---|---|---|
| PATENT NO. | : 7,091,330 B2 | Page 1 of 1 |
| APPLICATION NO. | : 09/873106 | |
| DATED | : August 15, 2006 | |
| INVENTOR(S) | : Ellis L. Reinherz et al. | |

It is certified that error appears in the above-identified patent and that said Letters Patent is hereby corrected as shown below:

Please insert at Column 1, line 3 before the "Related Applications" section the following paragraph:

--GOVERNMENT SUPPORT

The invention was supported, in whole or in part, by grants AI21226 and AI27581 from the National Institutes of Health. The Government has certain rights in the invention.--

Signed and Sealed this

Second Day of December, 2008

JON W. DUDAS
*Director of the United States Patent and Trademark Office*

SEQUENCE LISTING

<160> NUMBER OF SEQ ID NOS: 25

<210> SEQ ID NO 1
<211> LENGTH: 1299
<212> TYPE: DNA
<213> ORGANISM: Homo sapiens
<220> FEATURE:
<221> NAME/KEY: CDS
<222> LOCATION: (121)...(1143)

<400> SEQUENCE: 1

```
agtcctcttc cgggtgatgg cggcgggtgc cccggatgta gccctggcgc aagcatctct      60
tcttttttcc acctcgcctt ccgcggattc ccagcttgag aaacacctct ttgccccgtc     120 atg cca aag agg aaa gtg acc ttc caa ggc gtg gga gat gag gag gat       168
Met Pro Lys Arg Lys Val Thr Phe Gln Gly Val Gly Asp Glu Glu Asp
  1               5                  10                  15 gag gat gaa atc att gtc ccc aag aag aag ctg gtg gac cct gtg gct       216
Glu Asp Glu Ile Ile Val Pro Lys Lys Lys Leu Val Asp Pro Val Ala
             20                  25                  30 ggg tca ggg ggt cct ggg agc cgc ttt aaa ggc aaa cac tct ttg gat       264
Gly Ser Gly Gly Pro Gly Ser Arg Phe Lys Gly Lys His Ser Leu Asp
         35                  40                  45 agc gat gag gag gag gat gat gat gat ggg ggg tcc agc aaa tat gac       312
Ser Asp Glu Glu Glu Asp Asp Asp Asp Gly Gly Ser Ser Lys Tyr Asp
     50                  55                  60 atc ttg gcc tca gag gat gta gaa ggt cag gag gca gcc aca ctc ccc       360
Ile Leu Ala Ser Glu Asp Val Glu Gly Gln Glu Ala Ala Thr Leu Pro
 65                  70                  75                  80 agc gag ggg ggt ggt cgg atc aca ccc ttt aac ctg cag gag gag atg       408
Ser Glu Gly Gly Gly Arg Ile Thr Pro Phe Asn Leu Gln Glu Glu Met
                 85                  90                  95 gag gaa ggc cac ttt gat gcc gat ggc aac tac ttc ctg aac cgg gat       456
Glu Glu Gly His Phe Asp Ala Asp Gly Asn Tyr Phe Leu Asn Arg Asp
            100                 105                 110 gct cag atc cga gac agc tgg ctg gac aac att gac tgg gtg aag atc       504
Ala Gln Ile Arg Asp Ser Trp Leu Asp Asn Ile Asp Trp Val Lys Ile
        115                 120                 125 cgg gag cgg cca cct ggc cag cgc cag gcc tca gac tcg gag gag gag       552
Arg Glu Arg Pro Pro Gly Gln Arg Gln Ala Ser Asp Ser Glu Glu Glu
    130                 135                 140 gac agc ttg ggc cag acc tca atg agt gcc caa gcc ctc ttg gag gga       600
Asp Ser Leu Gly Gln Thr Ser Met Ser Ala Gln Ala Leu Leu Glu Gly
145                 150                 155                 160 ctt ttg gag ctc cta ttg cct aga gag aca gtg gct ggg gca ctg agg       648
Leu Leu Glu Leu Leu Leu Pro Arg Glu Thr Val Ala Gly Ala Leu Arg
                165                 170                 175 cgt ctg ggg gcc cga gga gga ggc aaa ggg aga aag ggg cct ggg caa       696
Arg Leu Gly Ala Arg Gly Gly Gly Lys Gly Arg Lys Gly Pro Gly Gln
            180                 185                 190 ccc agt tcc cct cag cgc ctg gac cgg ctc tcc ggg ttg gcc gac cag       744
Pro Ser Ser Pro Gln Arg Leu Asp Arg Leu Ser Gly Leu Ala Asp Gln
        195                 200                 205 atg gtg gcc cgg ggc aac ctt ggt gta tac cag gaa aca agg gaa cgg       792
Met Val Ala Arg Gly Asn Leu Gly Val Tyr Gln Glu Thr Arg Glu Arg
    210                 215                 220 ttg gct atg cgt ctg aag ggt ttg ggg tgt cag acc cta gga ccc cac       840
Leu Ala Met Arg Leu Lys Gly Leu Gly Cys Gln Thr Leu Gly Pro His
225                 230                 235                 240
```

```
                                                                -continued aat ccc aca ccc cca ccc tcc ctg gac atg ttc gct gag gag ttg gcg      888
Asn Pro Thr Pro Pro Pro Ser Leu Asp Met Phe Ala Glu Glu Leu Ala
            245                 250                 255 gag gag gaa ctg gag acc cca acc cct acc cag aga gga gaa gca gag      936
Glu Glu Glu Leu Glu Thr Pro Thr Pro Thr Gln Arg Gly Glu Ala Glu
        260                 265                 270 tcg cgg gga gat ggt ctg gtg gat gtg atg tgg gaa tat aag tgg gag      984
Ser Arg Gly Asp Gly Leu Val Asp Val Met Trp Glu Tyr Lys Trp Glu
    275                 280                 285 aac acg ggg gat gcc gag ctg tat ggg ccc ttc acc agc gcc cag atg     1032
Asn Thr Gly Asp Ala Glu Leu Tyr Gly Pro Phe Thr Ser Ala Gln Met
290                 295                 300 cag acc tgg gtg agt gaa ggc tac ttc ccg gac ggt gtt tat tgc cgg     1080
Gln Thr Trp Val Ser Glu Gly Tyr Phe Pro Asp Gly Val Tyr Cys Arg
305                 310                 315                 320 aag ctg gac ccc cct ggt ggt cag ttc tac aac tcc aaa cgc att gac     1128
Lys Leu Asp Pro Pro Gly Gly Gln Phe Tyr Asn Ser Lys Arg Ile Asp
            325                 330                 335 ttt gac ctc tac acc tgagcctgct gggggcccag tttggtgggc ccttctttcc     1183
Phe Asp Leu Tyr Thr
            340 tggactttgt ggaggaggca ccaagtgtct caggcagcga ggaaattgga ggccattttt   1243 cagtcaattt cccttttccca ataaaagcct tagttgtgta aaaaaaaaaa aaaaaa      1299

<210> SEQ ID NO 2
<211> LENGTH: 341
<212> TYPE: PRT
<213> ORGANISM: Homo sapiens

<400> SEQUENCE: 2

Met Pro Lys Arg Lys Val Thr Phe Gln Gly Val Gly Asp Glu Glu Asp
1               5                   10                  15

Glu Asp Glu Ile Ile Val Pro Lys Lys Lys Leu Val Asp Pro Val Ala
            20                  25                  30

Gly Ser Gly Gly Pro Gly Ser Arg Phe Lys Gly Lys His Ser Leu Asp
        35                  40                  45

Ser Asp Glu Glu Glu Asp Asp Asp Gly Gly Ser Ser Lys Tyr Asp
    50                  55                  60

Ile Leu Ala Ser Glu Asp Val Glu Gly Gln Glu Ala Ala Thr Leu Pro
65                  70                  75                  80

Ser Glu Gly Gly Gly Arg Ile Thr Pro Phe Asn Leu Gln Glu Glu Met
                85                  90                  95

Glu Glu Gly His Phe Asp Ala Asp Gly Asn Tyr Phe Leu Asn Arg Asp
            100                 105                 110

Ala Gln Ile Arg Asp Ser Trp Leu Asp Asn Ile Asp Trp Val Lys Ile
        115                 120                 125

Arg Glu Arg Pro Pro Gly Gln Arg Gln Ala Ser Asp Ser Glu Glu Glu
    130                 135                 140

Asp Ser Leu Gly Gln Thr Ser Met Ser Ala Gln Ala Leu Leu Glu Gly
145                 150                 155                 160

Leu Leu Glu Leu Leu Leu Pro Arg Glu Thr Val Ala Gly Ala Leu Arg
                165                 170                 175

Arg Leu Gly Ala Arg Gly Gly Lys Gly Arg Lys Gly Pro Gly Gln
            180                 185                 190

Pro Ser Ser Pro Gln Arg Leu Asp Arg Leu Ser Gly Leu Ala Asp Gln
        195                 200                 205
```

-continued

Met Val Ala Arg Gly Asn Leu Gly Val Tyr Gln Glu Thr Arg Glu Arg
        210                 215                 220

Leu Ala Met Arg Leu Lys Gly Leu Gly Cys Gln Thr Leu Gly Pro His
225                 230                 235                 240

Asn Pro Thr Pro Pro Ser Leu Asp Met Phe Ala Glu Glu Leu Ala
            245                 250                 255

Glu Glu Glu Leu Glu Thr Pro Thr Pro Thr Gln Arg Gly Glu Ala Glu
        260                 265                 270

Ser Arg Gly Asp Gly Leu Val Asp Val Met Trp Glu Tyr Lys Trp Glu
        275                 280                 285

Asn Thr Gly Asp Ala Glu Leu Tyr Gly Pro Phe Thr Ser Ala Gln Met
    290                 295                 300

Gln Thr Trp Val Ser Glu Gly Tyr Phe Pro Asp Gly Val Tyr Cys Arg
305                 310                 315                 320

Lys Leu Asp Pro Pro Gly Gly Gln Phe Tyr Asn Ser Lys Arg Ile Asp
                325                 330                 335

Phe Asp Leu Tyr Thr
            340

<210> SEQ ID NO 3
<211> LENGTH: 26
<212> TYPE: PRT
<213> ORGANISM: Homo sapiens

<400> SEQUENCE: 3

Gly Asp Ala Glu Leu Tyr Gly Pro Phe Thr Ser Ala Gln Met Gln Thr
1               5                   10                  15

Trp Val Ser Glu Gly Tyr Phe Pro Asp Gly
            20                  25

<210> SEQ ID NO 4
<211> LENGTH: 27
<212> TYPE: PRT
<213> ORGANISM: Caenorhabditis elegans

<400> SEQUENCE: 4

Gly Pro Asp Ser Glu Lys Tyr Gly Pro Tyr Met Ser Lys Asp Met Leu
1               5                   10                  15

Phe Trp Leu Gln Ala Gly Tyr Phe Asn Asp Gly
            20                  25

<210> SEQ ID NO 5
<211> LENGTH: 27
<212> TYPE: PRT
<213> ORGANISM: Caenorhabditis elegans

<400> SEQUENCE: 5

Asp Pro Thr Glu Thr Arg Arg Gly Pro Phe Pro Lys Asp Gln Met Asn
1               5                   10                  15

Val Trp Phe Lys Ala Gly Tyr Phe Thr Asp Glu
            20                  25

<210> SEQ ID NO 6
<211> LENGTH: 27
<212> TYPE: PRT
<213> ORGANISM: Caenorhabditis elegans

<400> SEQUENCE: 6

Asp Asp Arg Gly Thr Val Gln Gly Pro Tyr Gly Ala Ser Thr Val Leu
1               5                   10                  15

```
Asp Trp Tyr Gln Lys Gly Tyr Phe Ser Asp Asn
            20                  25

<210> SEQ ID NO 7
<211> LENGTH: 29
<212> TYPE: PRT
<213> ORGANISM: Saccharomyces cerevisiae

<400> SEQUENCE: 7

Asp Thr Gln Gly Gln Ile His Gly Pro Phe Thr Thr Gln Met Met Ser
1               5                   10                  15

Gln Trp Tyr Ile Gly Gly Leu Glu Tyr Phe Ala Ser Thr
            20                  25

<210> SEQ ID NO 8
<211> LENGTH: 27
<212> TYPE: PRT
<213> ORGANISM: Saccharomyces cerevisiae

<400> SEQUENCE: 8

Asp Ser Asn Gly Asn Ile Gln Gly Pro Phe Gly Thr Asn Asn Met Ser
1               5                   10                  15

Gln Trp Tyr Gln Gly Gly Tyr Phe Thr Pro Thr
            20                  25

<210> SEQ ID NO 9
<211> LENGTH: 17
<212> TYPE: PRT
<213> ORGANISM: Artificial Sequence
<220> FEATURE:
<223> OTHER INFORMATION: Motif in CD2 binding region of CD2BP2
<220> FEATURE:
<221> NAME/KEY: VARIANT
<222> LOCATION: 3, 4, 5, 6, 7, 8, 9, 10, 12, 13, 14
<223> OTHER INFORMATION: Xaa = Any Amino Acid

<400> SEQUENCE: 9

Gly Pro Xaa Xaa Xaa Xaa Xaa Xaa Xaa Trp Xaa Xaa Xaa Gly Thr
1               5                   10                  15

Phe

<210> SEQ ID NO 10
<211> LENGTH: 6
<212> TYPE: PRT
<213> ORGANISM: Artificial Sequence
<220> FEATURE:
<223> OTHER INFORMATION: CD2BP2 binding region

<400> SEQUENCE: 10

Pro Pro Pro Gly His Arg
1               5

<210> SEQ ID NO 11
<211> LENGTH: 70
<212> TYPE: PRT
<213> ORGANISM: Homo sapiens

<400> SEQUENCE: 11

Pro Pro Pro Pro Pro Gly His Arg Ser Gln Ala Pro Ser His Arg Pro
1               5                   10                  15

Pro Pro Pro Gly His Arg Val Gln His Gln Pro Gln Lys Arg Pro Pro
            20                  25                  30

Ala Pro Ser Gly Thr Gln Val His Gln Gln Lys Gly Pro Pro Leu Pro
```

```
                    35                  40                  45
Arg Pro Arg Val Gln Pro Lys Pro Pro His Gly Ala Ala Glu Asn Ser
    50                  55                  60

Leu Ser Pro Ser Ser Asn
65                  70
```

<210> SEQ ID NO 12
<211> LENGTH: 8
<212> TYPE: DNA
<213> ORGANISM: Artificial Sequence
<220> FEATURE:
<223> OTHER INFORMATION: Kozak consensus sequence

<400> SEQUENCE: 12 ccgccacc                                                                8

<210> SEQ ID NO 13
<211> LENGTH: 24
<212> TYPE: DNA
<213> ORGANISM: Artificial Sequence
<220> FEATURE:
<223> OTHER INFORMATION: Flag Epitope

<400> SEQUENCE: 13
gactacaagg acgacgatga caag                                             24

<210> SEQ ID NO 14
<211> LENGTH: 8
<212> TYPE: PRT
<213> ORGANISM: Artificial Sequence
<220> FEATURE:
<223> OTHER INFORMATION: Flag Epitope

<400> SEQUENCE: 14

```
Asp Tyr Lys Asp Asp Asp Asp Lys
  1               5
```

<210> SEQ ID NO 15
<211> LENGTH: 31
<212> TYPE: PRT
<213> ORGANISM: Gallus gallus
<220> FEATURE:
<223> OTHER INFORMATION: Flag Epitope

<400> SEQUENCE: 15

```
Trp Tyr Tyr Lys Asp Pro Gln Gly Glu Ile Gln Gly Pro Phe Ser Asn
  1               5                  10                  15

Gln Glu Met Ala Glu Trp Phe Gln Ala Gly Tyr Phe Thr Met Ser
                 20                  25                  30
```

<210> SEQ ID NO 16
<211> LENGTH: 38
<212> TYPE: PRT
<213> ORGANISM: Drosophila melanogaster
<220> FEATURE:
<223> OTHER INFORMATION: Flag Epitope

<400> SEQUENCE: 16

```
Glu Val Thr Trp Glu Phe Lys Trp Ser Gln Asp Glu Thr Asp Ile Gln
  1               5                  10                  15

Gly Pro Phe Ser Thr Glu Lys Met Leu Lys Trp Ser Gln Glu Asn Thr
                 20                  25                  30

Arg Tyr Phe Lys Asn Gly
                 35
```

-continued

```
<210> SEQ ID NO 17
<211> LENGTH: 34
<212> TYPE: PRT
<213> ORGANISM: Leishmania major
<220> FEATURE:
<223> OTHER INFORMATION: Flag Epitope

<400> SEQUENCE: 17

Val Trp Met Met Arg Trp Lys Ala Lys Pro Thr Val Gln His Gly Pro
 1               5                  10                  15

Phe Thr Asp Asp Ala Ile Gln Gln Trp Gly Arg Asp Gly Tyr Phe Gly
            20                  25                  30

Lys Lys

<210> SEQ ID NO 18
<211> LENGTH: 36
<212> TYPE: PRT
<213> ORGANISM: Caenorhabditis elegans
<220> FEATURE:
<223> OTHER INFORMATION: Flag Epitope

<400> SEQUENCE: 18

Val Ile Asp Thr Lys Trp His Tyr Leu Gly Pro Asp Ser Glu Lys Tyr
 1               5                  10                  15

Gly Pro Tyr Met Ser Lys Asp Met Leu Phe Trp Leu Gln Ala Gly Tyr
            20                  25                  30

Phe Asn Asp Gly
            35

<210> SEQ ID NO 19
<211> LENGTH: 35
<212> TYPE: PRT
<213> ORGANISM: Caenorhabditis elegans
<220> FEATURE:
<223> OTHER INFORMATION: Flag Epitope

<400> SEQUENCE: 19

Val Glu Ser Ser Trp Arg Tyr Ile Asp Thr Gln Gly Gln Ile His Gly
 1               5                  10                  15

Pro Phe Thr Ile Gln Met Met Ser Gln Trp Tyr Ile Gly Gly Tyr Phe
            20                  25                  30

Ala Ser Thr
        35

<210> SEQ ID NO 20
<211> LENGTH: 35
<212> TYPE: PRT
<213> ORGANISM: Saccharomyces cerevisiae
<220> FEATURE:
<223> OTHER INFORMATION: Flag Epitope

<400> SEQUENCE: 20

Ile Glu Ser Gln Trp Lys Tyr Ile Asp Ser Asn Gly Asn Ile Gln Gly
 1               5                  10                  15

Pro Phe Gly Thr Asn Asn Met Ser Gln Trp Tyr Gln Gly Gly Tyr Phe
            20                  25                  30

Thr Pro Thr
        35

<210> SEQ ID NO 21
<211> LENGTH: 31
```

<212> TYPE: PRT
<213> ORGANISM: Saccharomces pombe
<220> FEATURE:
<223> OTHER INFORMATION: Flag Epitope

<400> SEQUENCE: 21

```
Trp Leu Tyr Lys Asp Pro Gln Asn Asn Val Gln Gly Pro Phe Thr Gly
 1               5                  10                  15

Val Asp Met His Gln Trp Tyr Arg Ala Gly Tyr Phe Pro Leu Gly
             20                  25                  30
```

<210> SEQ ID NO 22
<211> LENGTH: 21
<212> TYPE: PRT
<213> ORGANISM: Homo sapiens
<220> FEATURE:
<223> OTHER INFORMATION: Flag Epitope

<400> SEQUENCE: 22

```
Pro Pro Pro Pro Gly His Arg Ser Gln Ala Pro Ser His Arg Pro Pro
 1               5                  10                  15

Pro Pro Gly His Arg
             20
```

<210> SEQ ID NO 23
<211> LENGTH: 62
<212> TYPE: PRT
<213> ORGANISM: Homo sapiens
<220> FEATURE:
<223> OTHER INFORMATION: Flag Epitope

<400> SEQUENCE: 23

```
Asp Val Met Trp Glu Tyr Lys Trp Glu Asn Thr Gly Asp Ala Glu Leu
 1               5                  10                  15

Tyr Gly Pro Phe Thr Ser Ala Gln Met Gln Thr Trp Val Ser Glu Gly
             20                  25                  30

Tyr Phe Pro Asp Gly Val Tyr Cys Arg Lys Leu Asp Pro Pro Gly Gly
         35                  40                  45

Gln Phe Tyr Asn Ser Lys Arg Ile Asp Phe Asp Leu Tyr Thr
     50                  55                  60
```

<210> SEQ ID NO 24
<211> LENGTH: 31
<212> TYPE: PRT
<213> ORGANISM: Homo sapiens
<220> FEATURE:
<223> OTHER INFORMATION: Flag Epitope

<400> SEQUENCE: 24

```
Trp Tyr Tyr Lys Asp Pro Gln Gly Glu Ile Gln Gly Pro Phe Asn Asn
 1               5                  10                  15

Gln Glu Met Ala Glu Trp Phe Gln Ala Gly Tyr Phe Thr Met Ser
             20                  25                  30
```

<210> SEQ ID NO 25
<211> LENGTH: 31
<212> TYPE: PRT
<213> ORGANISM: Homo sapiens
<220> FEATURE:
<223> OTHER INFORMATION: Flag Epitope -continued

```
<400> SEQUENCE: 25

Gln Trp Phe Ser Arg Ser Leu Ala Pro Cys Pro Gly Pro Phe Thr Thr
1               5                   10                  15

Gln Glu Met Ala Glu Trp Phe Gln Ala Gly Tyr Phe Ser Met Ser
            20                  25                  30
```